United States Patent
Golway et al.

(10) Patent No.: US 11,629,326 B2
(45) Date of Patent: Apr. 18, 2023

(54) MODULAR STORAGE UNITS FOR PERFUSION AND/OR INCUBATION OF ONE OR MORE SPECIMENS AND STORAGE ASSEMBLIES

(71) Applicant: Advanced Solutions Life Sciences, LLC, Louisville, KY (US)

(72) Inventors: Michael W. Golway, Louisville, KY (US); Scott Douglas Cambron, Louisville, KY (US)

(73) Assignee: Advanced Solutions Life Sciences, LLC, Louisville, KY (US)

( * ) Notice: Subject to any disclaimer, the term of this patent is extended or adjusted under 35 U.S.C. 154(b) by 282 days.

(21) Appl. No.: 16/502,795

(22) Filed: Jul. 3, 2019

(65) Prior Publication Data

US 2020/0010792 A1    Jan. 9, 2020

Related U.S. Application Data

(60) Provisional application No. 62/693,571, filed on Jul. 3, 2018.

(51) Int. Cl.
*C12M 1/00* (2006.01)
*C12M 1/34* (2006.01)
(Continued)

(52) U.S. Cl.
CPC ........... *C12M 41/14* (2013.01); *C12M 41/34* (2013.01); *C12M 41/36* (2013.01); *C12M 41/16* (2013.01); *C12M 41/48* (2013.01); *G01N 1/28* (2013.01)

(58) Field of Classification Search
None
See application file for complete search history.

(56) References Cited

U.S. PATENT DOCUMENTS 8,383,395 B2 * 2/2013 Hata ................. C12M 41/14
                                                         382/133
9,986,826 B1   6/2018 Melia
(Continued)

FOREIGN PATENT DOCUMENTS

CN        106916740    *  7/2017
CN        106916740 A    7/2017
(Continued)

OTHER PUBLICATIONS

Persson. Topical Humidified Carbon Dioxide to Keep the Open Surgical Wound Warm; Anesthesiology 2004; 101: 945-949 (Year: 2004).*

(Continued)

*Primary Examiner* — Donald R Spamer
*Assistant Examiner* — Nathan G Esperon
(74) *Attorney, Agent, or Firm* — Dinsmore & Shohl LLP

(57) ABSTRACT

A storage assembly for storing a plurality of specimens includes a frame, a plurality of modular storage units for perfusion and/or incubation of one or more specimens removably coupled to the frame, a sample transfer apparatus configured to retrieve a specimen holder from a chosen modular storage unit of the plurality of modular storage units, and a control unit communicatively coupled to the sample transfer apparatus. The control unit is configured to cause the sample transfer apparatus to retrieve a specimen from a modular storage unit of the plurality of modular storage units and deliver the specimen to a delivery position.

19 Claims, 31 Drawing Sheets

(51) Int. Cl.
*G01N 1/28* (2006.01)
*C12M 1/36* (2006.01)

(56) References Cited

U.S. PATENT DOCUMENTS

| | | | |
|---|---|---|---|
| 2005/0051723 A1* | 3/2005 | Neagle | C12M 41/48 250/306 |
| 2012/0028234 A1* | 2/2012 | Guertin | C12M 23/28 435/395 |
| 2012/0074121 A1 | 3/2012 | Gagas et al. | |
| 2013/0282171 A1 | 10/2013 | Kim | |
| 2014/0305227 A1* | 10/2014 | Johns | B04B 13/00 73/863.01 |
| 2015/0017711 A1 | 1/2015 | Bennett et al. | |
| 2015/0127145 A1 | 5/2015 | Kim | |
| 2015/0298321 A1 | 10/2015 | Gross et al. | |
| 2016/0145563 A1* | 5/2016 | Berteau | C12M 41/48 137/15.01 |
| 2017/0114316 A1* | 4/2017 | Newstrom | C12M 41/34 |

FOREIGN PATENT DOCUMENTS

| | | | |
|---|---|---|---|
| CN | 206375919 | * | 8/2017 |
| CN | 207294790 | * | 5/2018 |

OTHER PUBLICATIONS

International Search Report and Written Opinion of corresponding PCT/US2019/040562 dated Oct. 2, 2019.
Mikael Persson et al, "Topical Humidified Carbon Dioxide to Keep the Open Surgical Wound Warm" Anesthesiology 2004; 101: 945-9.
Extended European Search Report pertaining to corresponding European Patent Application No. 19831423.9 dated Mar. 30, 2022.

* cited by examiner

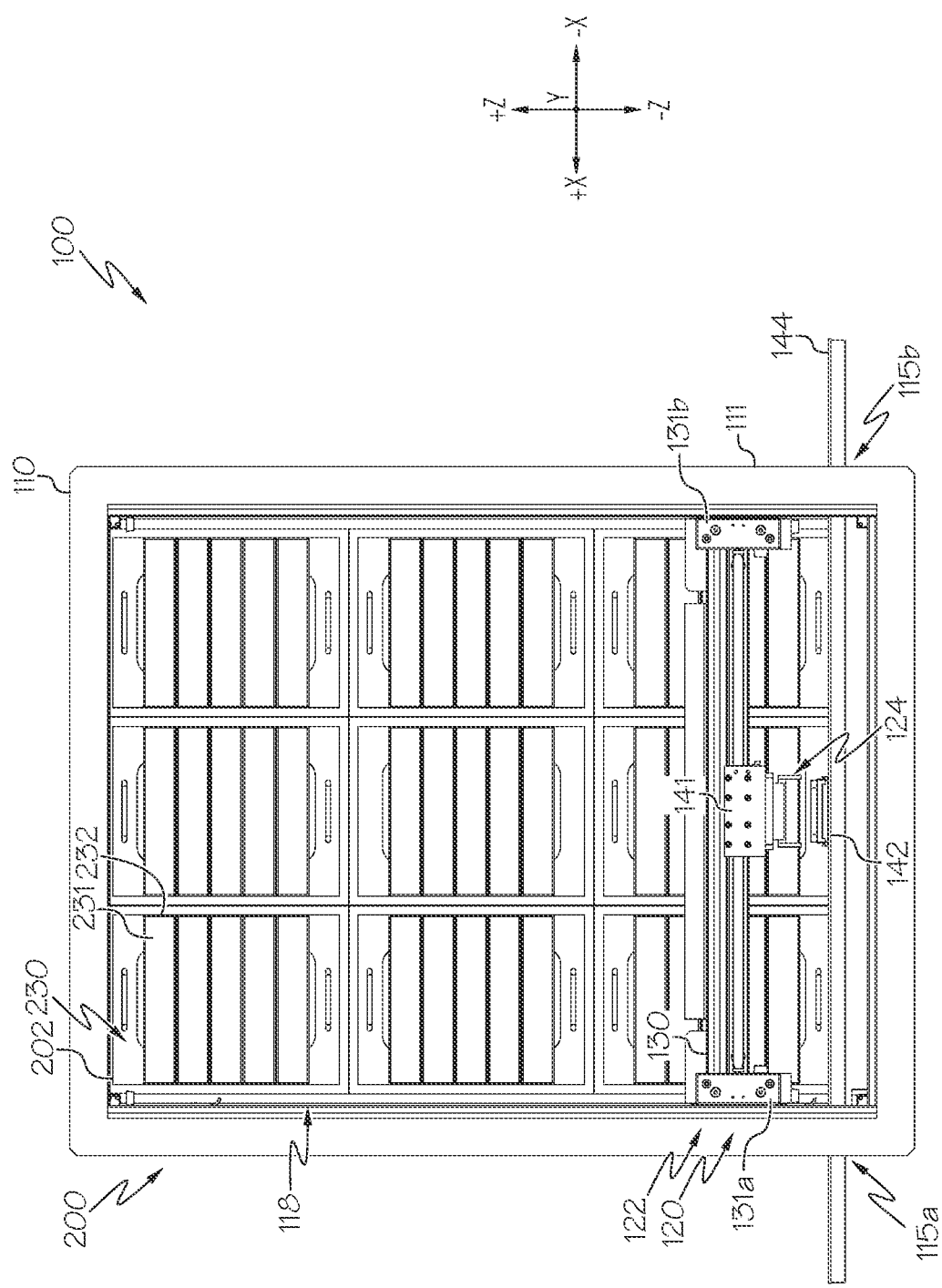

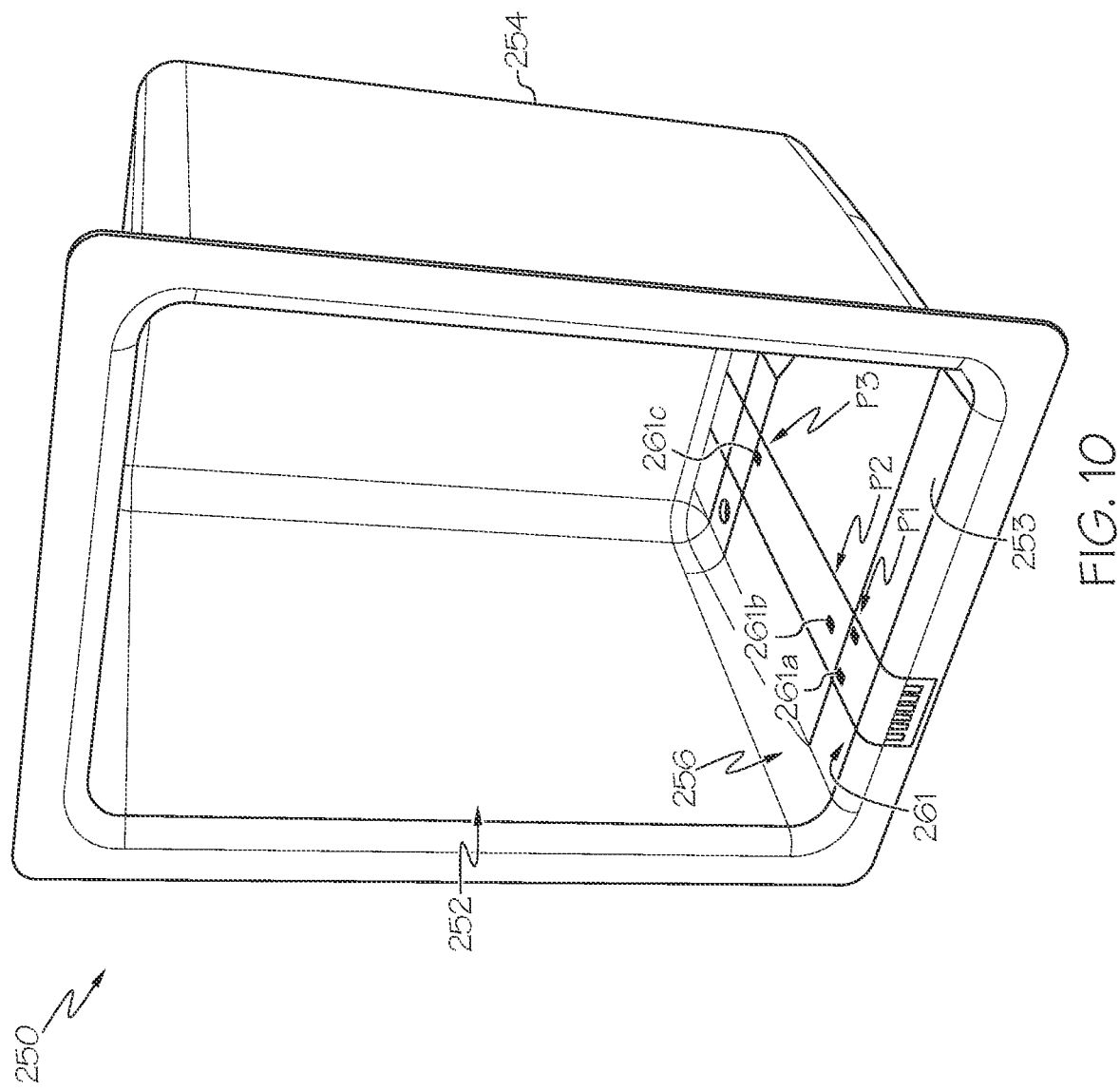

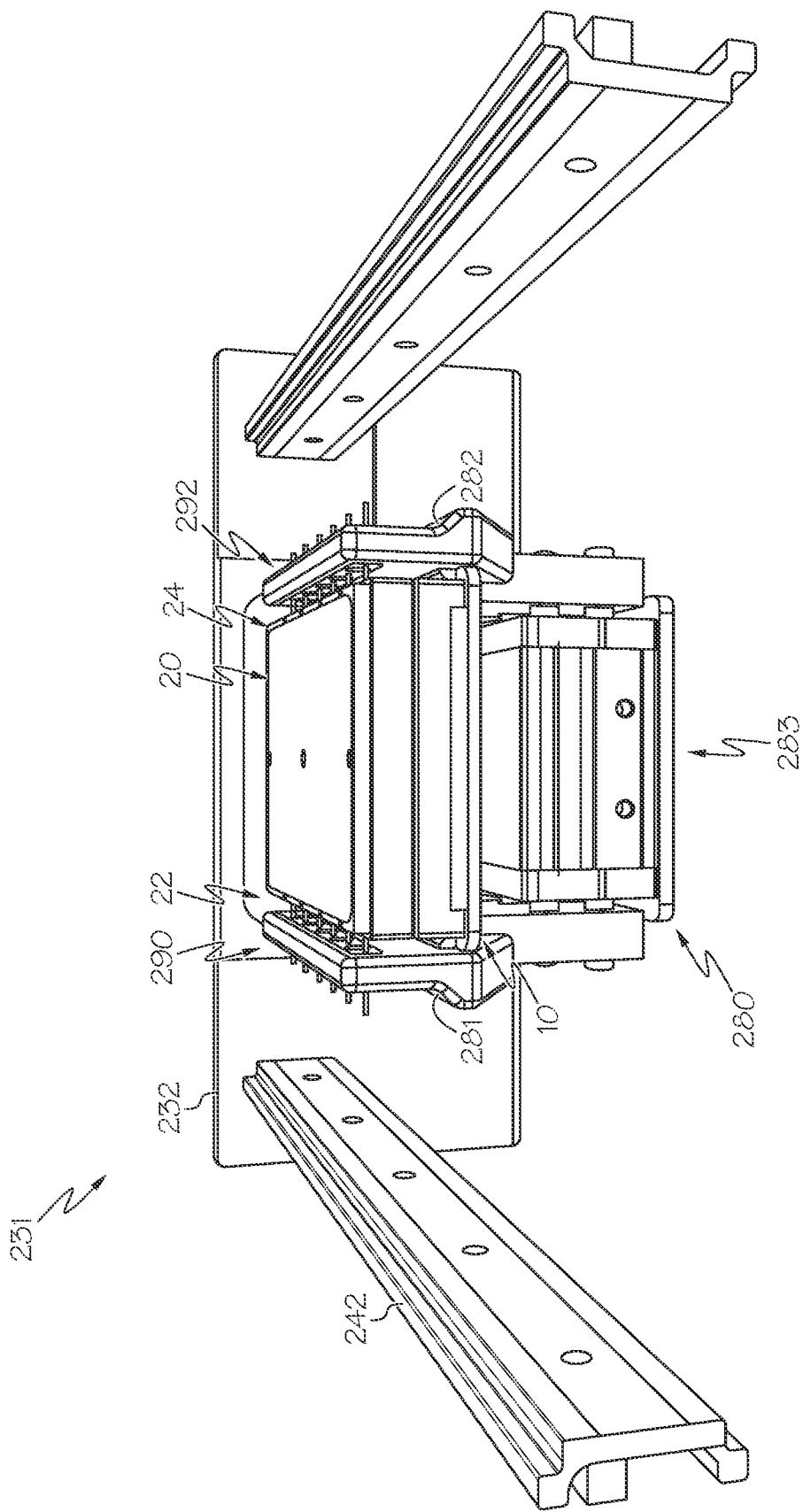

MODULAR STORAGE UNITS FOR PERFUSION AND/OR INCUBATION OF ONE OR MORE SPECIMENS AND STORAGE ASSEMBLIES

CROSS-REFERENCE TO RELATED APPLICATIONS

This application claims the benefit of U.S. Provisional Application Ser. No. 62/693,571, filed Jul. 3, 2018, entitled "System for Automated Environmentally Controlled Storage for Biological Specimen Containers," the entirety of which is incorporated by reference herein.

TECHNICAL FIELD

The present specification generally relates to storage units and assemblies for one or more specimens and, more specifically, modular storage units for perfusion and/or incubation of one or more specimens and storage assemblies for holding an array of such storage units.

BACKGROUND

In the biological sciences, an incubator may include a device used to grow and maintain microbiological or cell cultures for days or weeks at a time. The incubator is generally designed to maintain optimal temperature, relative humidity, and atmospheric gas concentration of biological viable gases such as carbon dioxide and oxygen within the controlled incubation environment. Incubators have been used in experimental work in cell biology, microbiology, and molecular biology.

Typical incubators are insulated enclosures that employ temperature control up to 60° C. The most commonly used temperature both for bacteria as well as for mammalian cells is approximately 37° C., as such organisms tend to grow well under such conditions. Some incubators may also control humidity and carbon dioxide concentrations. Such control may be beneficial in in the culturing of mammalian cells, where the relative humidity is typically >80% to prevent evaporation and a slightly acidic pH is achieved by maintaining a carbon dioxide level of approximately 5%.

The implementation of robotic lab automation equipment has become more prevalent in the fields pharmaceuticals, microbiology, cell culture, and tissue engineering. The ability to effectively incubate tissue constructs and cultures within commercially available specimen containers such as but not limited to petri dishes and multi-well plates are commonly employed on a benchtop where the lab scientist can open a door to the incubation platform and manually place samples on a shelf in the environmentally controlled system.

However, traditional incubators do not provide for different incubation and/or perfusion environments simultaneously. Moreover, traditional incubators are not modular in that they can be adjusted to fit varying types of specimens, containers, etc. Additionally, traditional incubators are not configured to provide an automated robotic workflow that allows a user to select specific incubation positions and/or times. Accordingly, a need exists for alternative storage units for perfusion and/or incubation of one or more specimens and storage assemblies for holding the same.

SUMMARY

In a first aspect, a storage unit for perfusion of one or more specimens includes an enclosure, an automated drawer assembly, a control unit, and one or more perfusion actuation platforms. The automated drawer assembly includes a faceplate mounted to the enclosure and one or more drawers. The control unit is communicatively coupled to the automated drawer assembly to control opening and closing of the one or more drawers. The one or more perfusion actuation platforms are configured to fluidically couple one or more specimen holders positioned within the one or more drawers to a media reservoir.

In a second aspect according to the first aspect, further including an incubation liner configured for heating and/or insulating the enclosure, wherein the incubation liner is communicatively coupled to the control unit.

In a third aspect according to either the first or the second aspects, further including an environmental control assembly communicatively coupled to the control unit and configured to control humidity, temperature, biological gas concentrations, perfusion parameters, or combinations thereof.

In a fourth aspect according to the third aspect, wherein the environmental control assembly comprises a bubbler system for humidifying dry carbon dioxide.

In a fifth aspect according to any preceding aspect, wherein the faceplate is magnetically coupled to the enclosure.

In a sixth aspect according to any preceding aspect, wherein the one or more drawers include a first drawer and a second drawer, and the one or more perfusion actuation platforms include a first perfusion actuation platform configured to fluidically couple a first specimen holder positioned within the first drawer to the media reservoir, and a second perfusion actuation platform configured to fluidically couple a second specimen holder positioned within the second drawer to the media reservoir.

In a seventh aspect according to any preceding aspect, wherein a perfusion actuation platform of the one or more perfusion actuation platforms includes a fluid inlet portion for delivery fluid to a fluidic manifold assembly of a specimen holder, a fluid outlet portion for retrieval of waste fluid from the fluidic manifold assembly of the specimen holder, and an actuator coupled to the fluid inlet portion and the fluid outlet portion and configured to move the fluid inlet portion and the fluid outlet portion between a closed position and an open position.

In an eighth aspect, a modular storage unit for incubation and/or perfusion of one or more specimens includes an enclosure, an automated drawer assembly, a control unit, and an environmental control assembly. The automated drawer assembly includes a replaceable faceplate mounted to the enclosure, the replaceable faceplate defining a number of drawer ports, and one or more drawers corresponding to the number of drawer ports in the replaceable faceplate. The control unit is communicatively coupled to the automated drawer assembly to control opening and closing of the one or more drawers. The environmental control assembly is communicatively coupled to the control unit and configured to control humidity, temperature, biological gas concentrations, perfusion parameters, or combinations thereof.

In a ninth aspect according to the eighth aspect, wherein the environmental control assembly comprises an incubation liner configured for heating and/or insulating the enclosure.

In a tenth aspect according to the ninth aspect, wherein the incubation liner defines a fluid reservoir and the incubation liner includes one or more fluid sensors communicatively coupled to the control unit, wherein the one or more fluid sensors output a fluid level signal indicative of a fluid level within the fluid reservoir.

In an eleventh aspect according to the tenth aspect, wherein the environmental control assembly includes a bubbler system for humidifying dry carbon dioxide.

In a twelfth aspect according to any of the eighth through the eleventh aspects, wherein the replaceable faceplate is magnetically coupled to the enclosure.

In a thirteenth aspect according to any of the eighth through the twelfth aspects, wherein the one or more drawers include at least two drawers.

In a fourteenth aspect according to any of the eighth through the thirteenth aspects, further including a user interface device communicatively coupled to the control unit and configured to receive a user input to control operation of the modular storage unit.

In a fifteenth aspect, a storage assembly for storing a plurality of specimens includes a frame, a plurality of modular storage units for perfusion and/or incubation of one or more specimens removably coupled to the frame, a sample transfer apparatus configured to retrieve a specimen holder from a chosen modular storage unit of the plurality of modular storage units, and a control unit communicatively coupled to the sample transfer apparatus. The control unit is configured to cause the sample transfer apparatus to retrieve a specimen from a modular storage unit of the plurality of modular storage units and deliver the specimen to a delivery position.

In a sixteenth aspect according to the fifteenth aspect, wherein the frame defines an enclosure within which the plurality of modular storage units and the sample transfer apparatus are positioned.

In a seventeenth aspect according to either the fifteenth aspect or the sixteenth aspect, wherein the plurality of modular storage units are arranged in an array including a plurality of rows and a plurality of columns.

In an eighteenth aspect according to any of the fifteenth through the seventeenth aspects, wherein the modular storage unit of the plurality of modular storage units includes an enclosure, an automated drawer assembly communicatively coupled to the control unit, the automated drawer assembly including a faceplate mounted to the enclosure, and one or more drawers.

In a nineteenth aspect according to any of the fifteenth through the eighteenth aspects, wherein each of the plurality of modular storage units comprises an environmental control assembly communicatively coupled to the control unit and configured to control humidity, temperature, biological gas concentrations, perfusion, or combinations thereof.

In a twentieth aspect according to any of the fifteenth through the nineteenth aspects, wherein the sample transfer apparatus includes a gripping device configured to grip and release the specimen holder, a two dimensional gantry arranged to move the gripping device between a closed position for retrieving the specimen holder and a released position to release the specimen holder, and a conveyor configured to move the specimen holder when placed thereon by the gripping device to a position outside of the frame.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 1C depicts a front view of the storage assembly of FIG. 1A, according to one or more embodiments shown and described herein;

FIG. 10 depicts an insulation liner of a modular storage unit, according to one or more embodiments shown and described herein;

FIG. 13C illustrates the perfusion actuation apparatus of FIG. 13B in a closed position, according to one or more embodiments shown and described herein.

DETAILED DESCRIPTION

The figures generally depict various embodiments of storage assemblies for storing an array of modular storage units. The array of modular storage units may be configured for incubation and/or perfusion of one or more specimens stored therein. A user may adjust a base assembly of a modular storage unit for application in either perfusion and/or incubation environments. A storage assembly may include a frame that may support the array of modular storage units. Each of the modular storage units may be arranged and rearranged on the frame by the user as desired. Each of the modular storage units may be docked into a control system of the storage assembly to allow for centralized control and adjustment of an incubation or perfusion environment for each of the modular storage units, such that each modular storage unit may have a different incubation and/or perfusion environment(s). Additionally, the storage assembly may provide an automated robotic workflow wherein a user may input a preset workflow protocol, and the storage assembly may arrange and rearrange specimens among the plurality of modular storage units in accordance with the preset workflow protocol. In yet further embodiments, the storage assembly may be integrated into a biological printing platform, such that printed biological specimens may be automatically transferred between the biological printing platform and the storage assembly. For example, the biological printing platform may print a biological specimen (e.g., a three-dimensional printed cellular structure) into a specimen holder (e.g., well-plate, petri dish, or the like), which may then be transferred automatically (e.g., by a robotic arm of the biological printing platform) to the storage assembly which may then store the specimen holder per user-programmed or preset instructions. Various embodiments of the storage assembly and the modular storage units will be described in more detail herein.

Figure 1A:
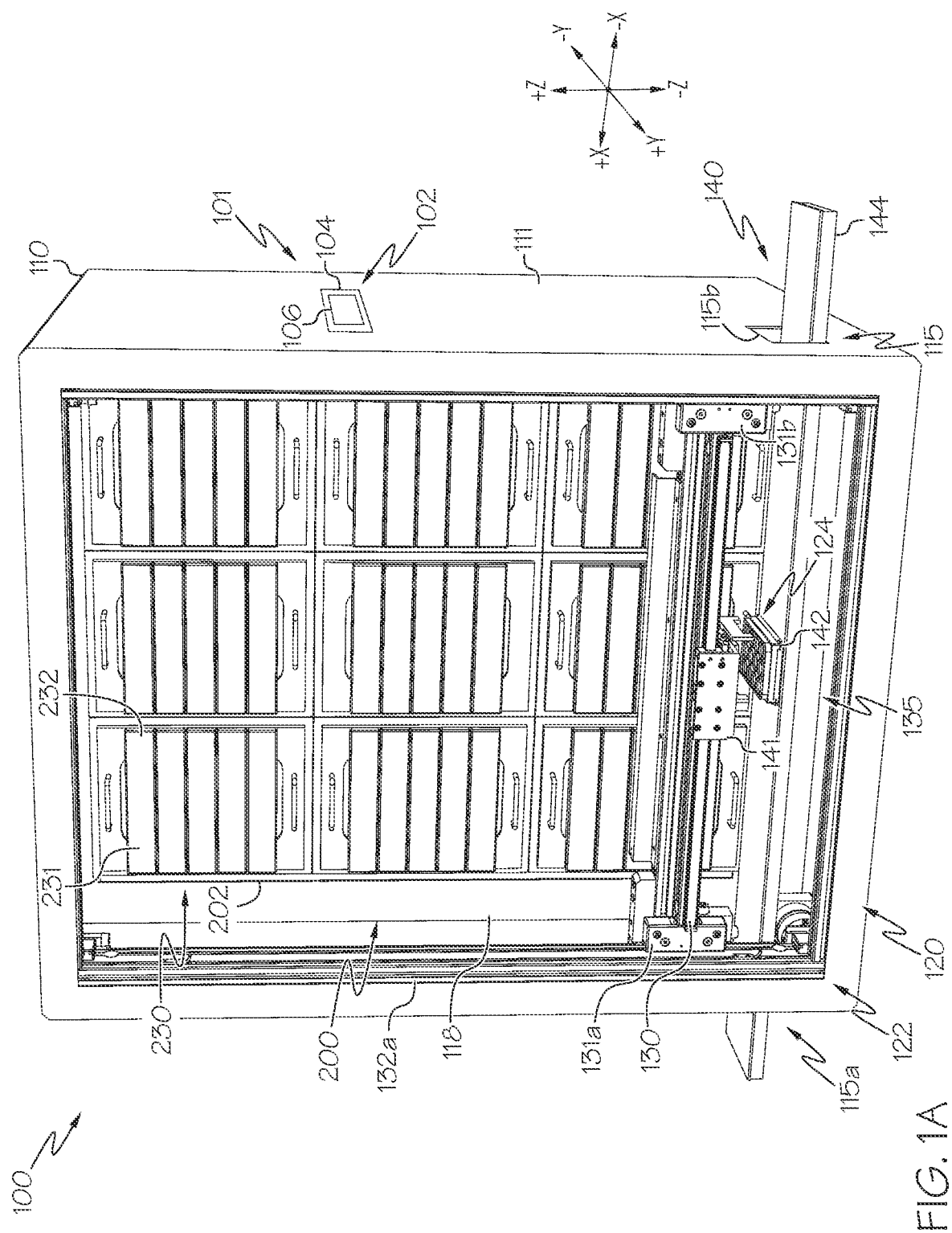
FIG. 1A schematically depicts a perspective view of a storage assembly for storing an array of modular storage units therein, according to one or more embodiments shown and described herein.
Figure 1B:
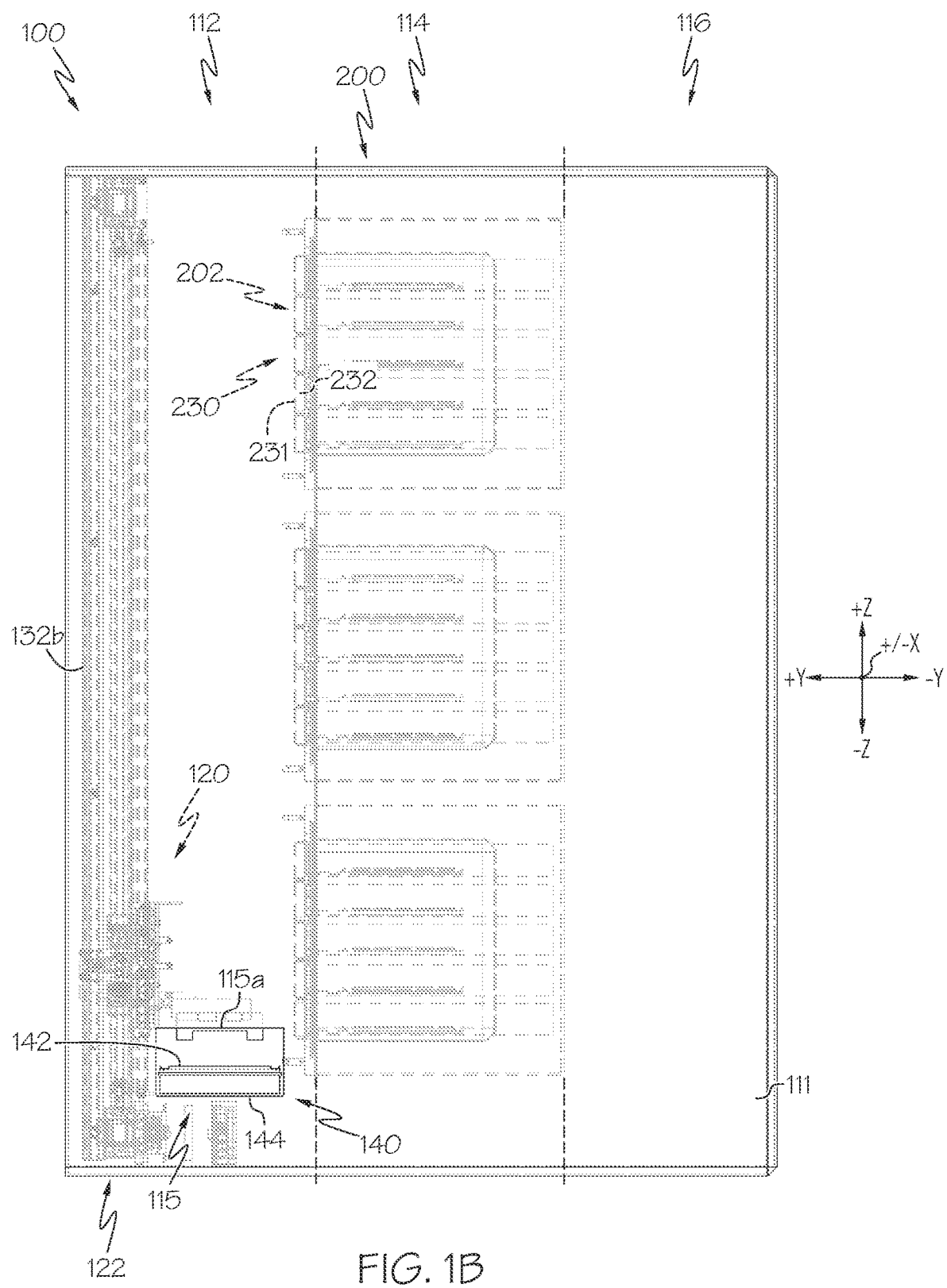
FIG. 1B schematically depicts a side view of the storage assembly of FIG. 1A, according to one or more embodiments shown and described herein

Referring now to FIGS. 1A-1C, a storage assembly 100 for storing a plurality of specimens is depicted. As used herein, the term specimen may refer to any biological specimen including, but not limited, three-dimensional printed biological constructs, bacteria, viruses, combinations thereof, or the like. In the illustrated embodiment, the storage assembly 100 includes a control system 101, a frame 110, a plurality of modular storage units 200 arranged in an array, and a sample transfer apparatus 120.

Figure 2:
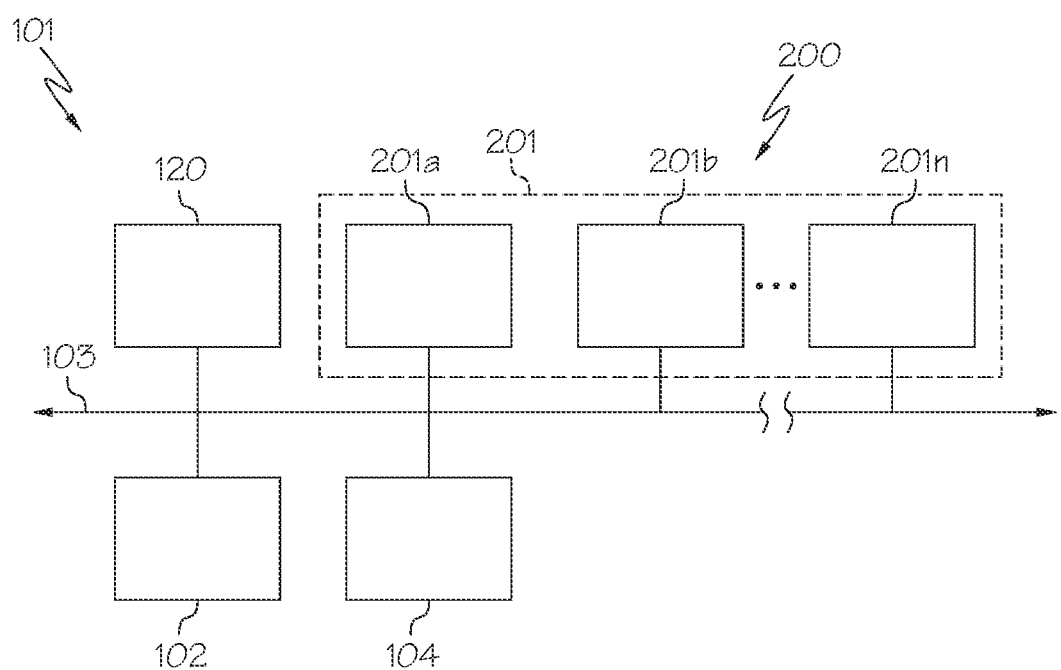
FIG. 2 schematically depicts communication between various components of the storage assembly, according to one or more embodiments shown and described herein.

FIG. 2 schematically illustrates the control system 101 for communicating with and/or controlling various components of the storage assembly 100 as will be described in greater detail herein. The control system 101 may include a communication path 103, a control unit 102, a user interface device 104, and the plurality of modular storage units 200. As will be described in greater detail herein, each of the modular storage units 200 may include an electrical communication harness 201, which may be plugged into the communication path 103. Any number of modular storage units 200 may be assembled to the control system 101 through their respective electrical communication harnesses (e.g., 201a, 201b, . . . 201n).

The various modules of the control system 101 may be communicatively coupled to one another over the communication path 103. The communication path 103 may be a bus, such as, for example, a CAN bus, a fieldbus or the like. The communication path 103 may be formed from any medium that is capable of transmitting a signal such as, for example, conductive wires, conductive traces, optical waveguides, or the like. Moreover, the communication path 103 may be formed from a combination of mediums capable of transmitting signals. In some embodiments, the communication path 103 includes a combination of conductive traces, conductive wires, connectors, and buses that cooperate to permit the transmission of electrical data signals between the various components of the components such as processors, memories, sensors, user interface devices, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The control unit 102 can be any type of computing device and includes one or more processors and one or more memory modules. The one or more processors may include any device capable of executing machine-readable instructions stored on a non-transitory computer-readable medium, such as those stored on the one or more memory modules. Accordingly, each of the one or more processors may include a controller, an integrated circuit, a microchip, a computer, and/or any other computing device.

The one or more memory modules of the control unit 102 are communicatively coupled to the one or more processors. The one or more memory modules may be configured as volatile and/or nonvolatile memory and, as such, may include random access memory (including SRAM, DRAM, and/or other types of RAM), flash memory, secure digital (SD) memory, registers, compact discs (CD), digital versatile discs (DVD), and/or other types of non-transitory computer-readable mediums. Depending on the particular embodiment, these non-transitory computer-readable mediums may reside within the control unit 102 and/or external to the control unit 102. The one or more memory modules may be configured to store logic (i.e., machine readable instructions) that, when executed by the one or more processors, allow the control unit 102 to individually control environmental and/or perfusion conditions of the plurality of modular storage units 200, store a specimen in a predetermined location within a specific modular storage unit 202, retrieve a stored specimen from a specific modular storage unit 202, transfer a stored specimen between modular storage units, or combinations thereof.

The user interface device 104 may be any device, which allows a user to communicate with the control unit 102 to control operation of the storage assembly 100. For example, the user interface device 104 may include, for example, a display and/or one or more user interface controls. The display may be, for example and without limitation, any liquid crystal display (LCD), light emitting diode (LED) display, electronic ink (e-ink) display, or the like that can display information to a user. In some embodiments, the display may be configured as an interactive display that can receive user inputs (e.g., a touch screen display or the like). The one or more user interface controls may be hardware components that receive inputs from a user and transmit signals corresponding to the inputs, such as a keyboard, a mouse, a joystick, a touch screen, a remote control, a pointing device, a video input device, an audio input device, and/or the like. In some embodiments, the display and one or more of the user interface controls may be combined into a single device, such as a touchscreen display 106 such as illustrated in FIG. 1A or the like. The display and/or the one or more user interface controls may be used, for example, to allow a user to interact with the storage assembly 100 to input environmental or perfusion settings for the one or more of the plurality of modular storage units 200, input an automated robotic workflow protocol for a particular sample being stored within the storage assembly 100, or the like.

Referring again to FIGS. 1A-1C and as noted above, the storage assembly 100 includes a frame 110, as shown in FIG. 1B, the frame 110 may define parallel corridors or zones including a transfer corridor 112, a storage corridor 114, and a maintenance corridor 116. The transfer corridor 112 may define a region in which a specimen carrier is transferred to and from a particular modular storage unit 202 and/or into and out of the frame 110 of the storage assembly 100. The transfer corridor 112 may include an access door, not shown, to allow manual access into and out of the frame 110 to, for example, replace a modular storage unit 202. The maintenance corridor 116 may be positioned on a backside of the storage assembly 100 such that the storage corridor 114 is positioned between the transfer corridor 112 and the maintenance corridor 116. In some embodiments, the storage corridor 116 may extend beneath the transfer corridor 112 and the storage corridor 114. The maintenance corridor 116 may include access electrical connections, fluidic connections, or the like to allow an operator to ensure proper maintenance and connections. Accordingly, an access door may also be provided to access the maintenance corridor 116. For example, the maintenance corridor may house all motor control hardware and/or instrumentation for the sample transfer apparatus 120, the control system hardware for communication and/or control of the various actuators, and environmental controls for incubation and/or perfusion, any ancillary hardware to support the plurality of modular storage units 200 and/or the sample transfer apparatus 120, and fluid sources such as pressurized gas, water, culture media, culture media additives, etc., and pneumatic tubing/plumbing for fluidically coupling the fluid sources to the plurality of modular storage units 200. From the maintenance corridor 116, an operator or technician may access the electrical communication harnesses 201 of the plurality of modular storage units 200.

Figure 1D:
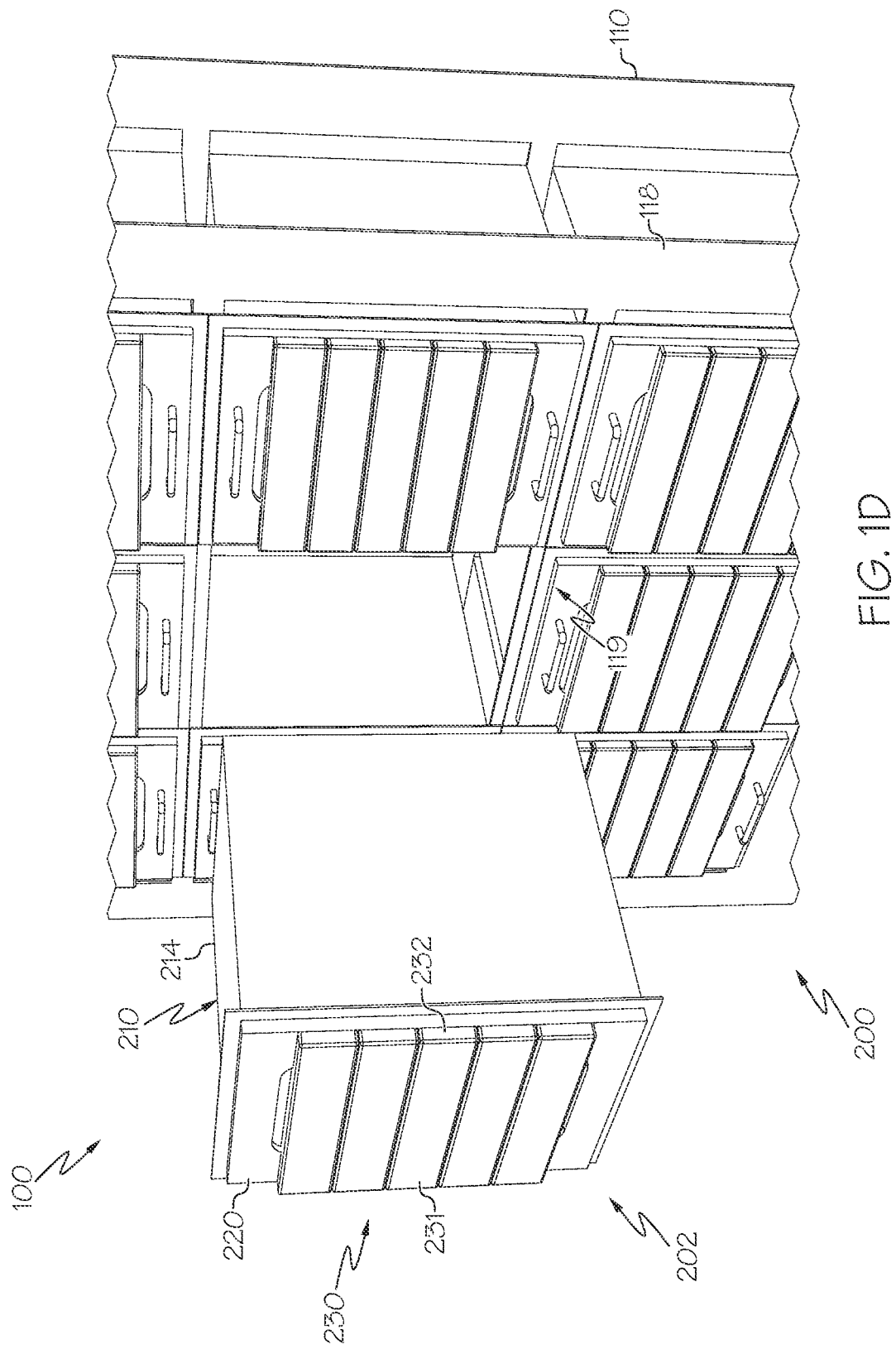
FIG. 1D depicts a modular storage unit being placed within the storage assembly of FIG. 1A, according to one or more embodiments shown and described herein.

The storage corridor 114 may include a storage compartment array 118 that defines a plurality of openings 119 into which each of the plurality of modular storage units 200 may rest. For example, the storage compartment array 118 may provide a shelf structure to support and provide separation between the plurality of modular storage units 200. FIG. 1D illustrates a modular storage unit 202 partially inserted into an opening 119 of the storage compartment array 118. The plurality of modular storage units 200 may be configured for incubation, perfusion, or any combination thereof. For example, a portion of the modular storage units 200 may be configured for incubation and another portion of the modular storage units 200 may be configured for perfusion. However, each of the plurality of modular storage units 200 may have a similar size and shape such that any type of modular storage unit 202 (e.g., a perfusion type, an incubation type, or a combination incubation/perfusion storage unit) may be inserted into any of the compartments of the storage compartment array 118. Each of the modular storage units 200 may be swapped out or moved to accommodate any perfusion and/or incubation needs of a user or a particular specimen. Various embodiments of the modular storage units 200 will be discussed in greater detail below. It is noted that the storage compartment array 118 may provide spacing for a plurality of rows (e.g., 3 rows) and a plurality of columns (e.g., 3 columns) of modular storage units 200. However, it is contemplated that a different array with greater and/or few rows and columns are contemplated and possible without departing from the scope of the present disclosure.

In some embodiments, the transfer corridor 112, the storage corridor 114, and/or the maintenance corridor 116 may include air filtration system (not shown) such as a HEPA or ULPA filtration system. An air filtration system may recirculate air frame 110 aid in maintaining a clean, dust free environment within the frame 110 of the storage assembly.

The frame 110 may further define one or more entry/egress ports 115 formed within a sidewall 111 of the frame 110. The one or more entry/egress ports 115 may allow for the sample transfer apparatus 120 to move a specimen holder 10 into and out of the frame 110. Other than the one or more entry/egress ports 115, the frame 110 may provide an enclosed environment within the storage assembly 100. Such closed environment may aid in preserving environmental settings within each of the plurality of modular storage units 200. In some embodiments, the one or more entry/egress ports 115 may caps, plugs, doors, or the like to allow for sealing of the one or more entry/egress ports 115.

Figure 3:
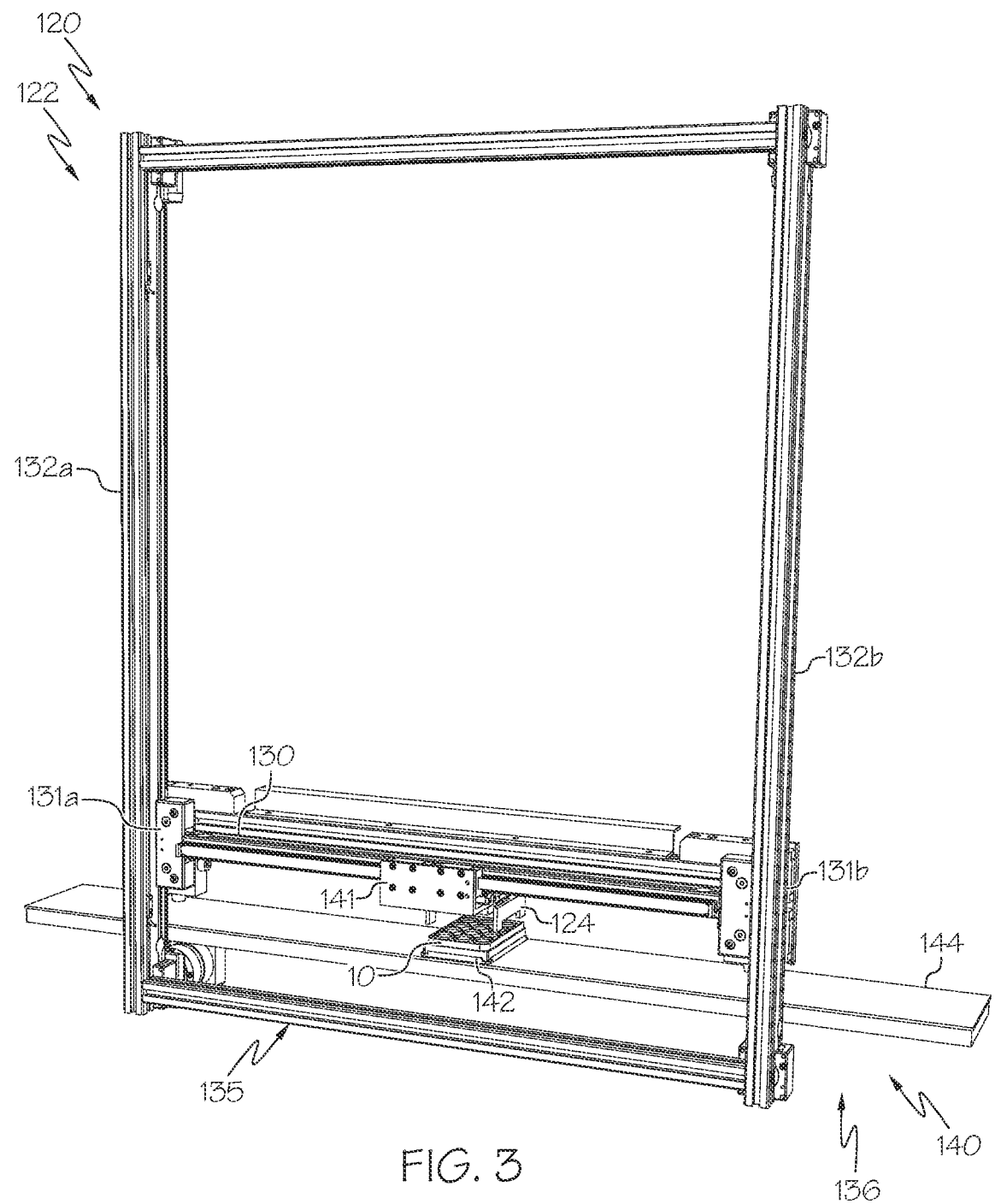
FIG. 3 depicts a sample transfer apparatus in isolation from the storage assembly of FIG. 1, according to one or more embodiments shown and described herein.

The sample transfer apparatus 120 may be communicatively coupled to the control unit 102 so as to allow the control unit 102 to actuate the sample transfer apparatus 120 to, for example, retrieve a specimen holder 10 from one of the plurality of storage units, deliver a specimen holder 10 to one of the plurality of storage units, deliver a specimen holder 10 to a position outside of the frame 110, and retrieve a specimen holder 10 from outside of the frame 110. FIG. 3 depicts the sample transfer apparatus 120 in isolation from the storage assembly 100. The sample transfer apparatus 120 may include a two-dimensional gantry 122, a gripping device 124, and a conveyor 140. Movement of each of these components may be accomplished through actuation of one or more actuators controlled by the control unit 102.

As illustrated in FIG. 1A-1C, the two-dimensional gantry 122 may be arranged within transfer corridor 112 of the frame 110 and configured to move the gripping device 124 within the X-Z Plane of the depicted coordinate axes. Referring also to FIG. 3, to facilitate motion if the gripping device 124 in the X direction of the depicted coordinate axes, the two-dimensional gantry 122 may include a lateral rail 130 to which the gripping device 124 is slidably coupled. An actuator (e.g., a linear actuator) may move the gripping device 124 along the lateral rail 130 in the +/−X direction to position the lateral rail 130 at a desired lateral position.

To facilitate motion of the gripping device 124 in the +/−Z direction of the depicted coordinate axes, the two-dimensional gantry 122 may include a first vertical rail 132a and a second vertical rail 132b positioned parallel to and spaced from the first vertical rail 132a. A first end 131a of the lateral rail 130 may be slidably coupled to the first vertical rail 132a and the second end 131b of the lateral rail 130 may be slidably coupled to the second vertical rail 132b. One or more actuators (not shown) may be operable to slide the lateral rail 130 along the first vertical rail 132a and the second vertical rail 132b to a desired position, thus positioning the gripping device 124 in the desired vertical position.

In some embodiments, instead of a two dimensional gantry 122, the sample transfer apparatus 120 may include any number of actuators for moving the gripping device 124 to a desired location. Such actuators may include a mechanical screw drive, electromechanical linear motors, mechanical rack and pinion drive systems, or the like. In some embodiments the two dimensional gantry 122 may be belt driven.

The gripping device 124 may be slidably coupled to the lateral rail 130 through a bracket 141. The gripping device 124 may be any device configured to securely engage and move a specimen holder 10 (e.g., petri dish, well plate, tissue culture flask, or the like). For example, FIG. 3 illustrates that specimen holder 10 as a well plate. The gripping device 124 may be an actuatable clamp or similar device that is able to engage opposite sides of the specimen holder 10. The gripping device 124 may be pneumatically, mechanically (e.g., via drive screws, belts, gears, etc.), hydraulically, or electrically (e.g., via solenoids) actuated between a closed position, wherein the gripping device 124 is able to grip the specimen holder 10 and a released position, wherein the gripping device 124 is able to release the specimen holder 10 at a desired position. The control unit 102 is configured to control operation of the gripping device 124 to grip and/or release the specimen holder 10.

The conveyor 140 may be communicatively coupled to the control unit 102 such that the control unit 102 may control motion of the conveyor 140. The conveyor 140 may be any device configured to move a specimen holder 10 positioned thereon into and out of the frame 110 of the storage assembly 100 through the one or more entry/egress 115 ports. It is noted that while two entry/egress ports 115 are depicted, there may be any number of entry/egress ports and conveyors for conveying a specimen holder into and out of the storage assembly 100.

In the depicted embodiment of FIG. 3, the conveyor 140 includes a delivery platen 142 configured to support a specimen holder 10 therein. For example, the delivery platen 142 may be shaped such that the specimen holder 10 partially nests within the delivery platen 142 to ensure proper alignment for pick-up/drop-off by the gripping device 124. The delivery platen 142 may be coupled to a rail 144 that is configured to move the delivery platen 142 laterally into and out of the frame 110 of the storage assembly 100 through the one or more entry/egress ports 115. For example, the rail 144 may extend through a first entry/egress port 115a on a first side of the frame 110 and a second entry/egress port 115b on a second side of the frame 110. In some embodiments, the frame 110 may only include one entry/egress port, such that the rail 144 extends through only one side of the frame 110. The delivery platen 142 may be driven along the rail 144 by an actuator (not shown) to cause the delivery platen 142 to pass into or out of the entry/egress port 115 (e.g., either the first entry/egress port 115a or the second entry/egress port 115b). It is noted that the gripping device 124 may, when not engaged with or in the process of the engaging a specimen holder 10, sit in a safe position above the conveyor 140 and the drawers of the plurality of modular storage units 200 so as not to block movement of the conveyor 140. In embodiments, the conveyor 140 may be driven via any actuators including but not limited to belts, screw drives, electromechanical linear motors, rack and pinion drive systems, and the like.

Figure 4A:
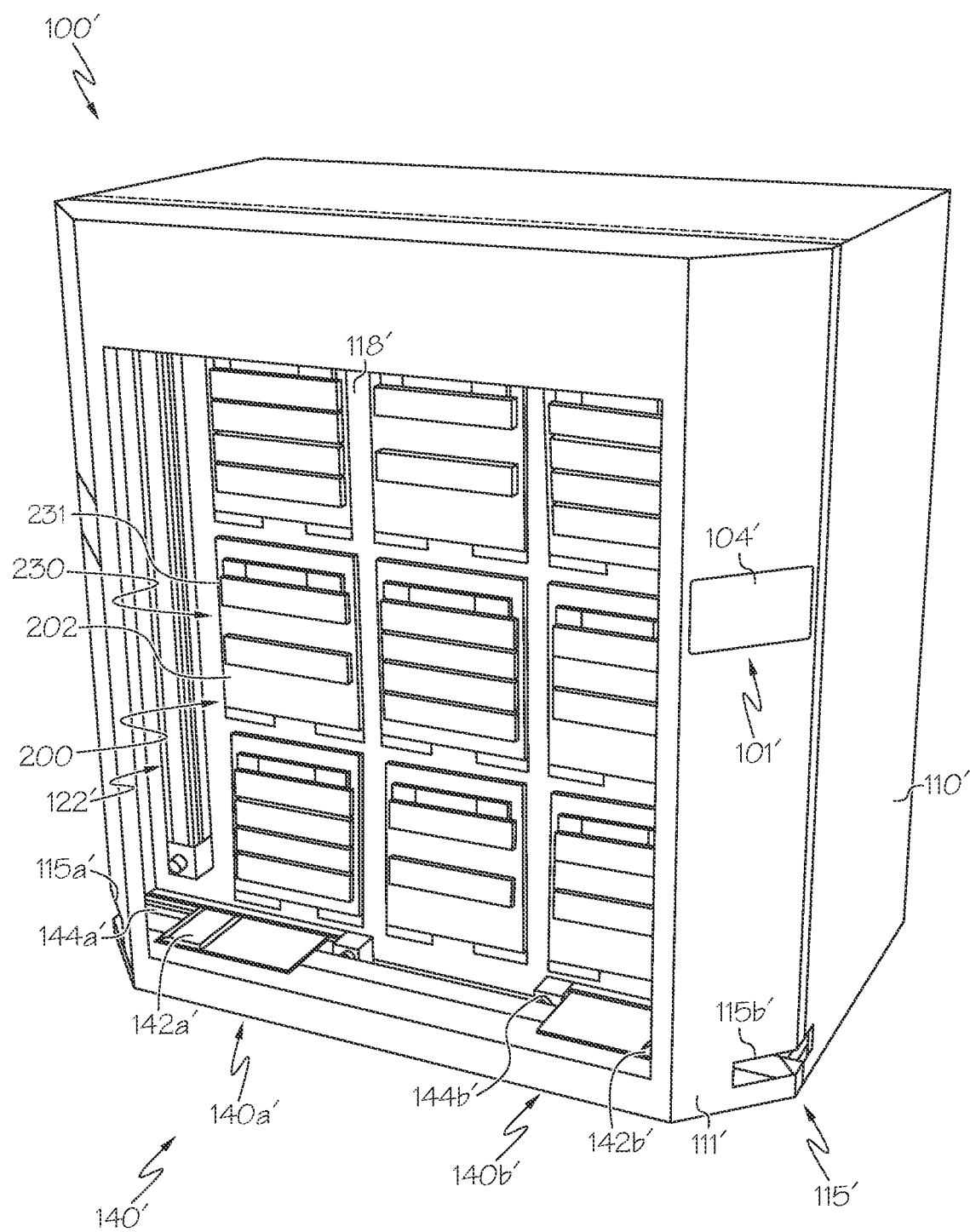
FIG. 4A a perspective view of a storage assembly for storing an array of modular storage units therein, according to one or more embodiments shown and described herein.
Figure 4B:
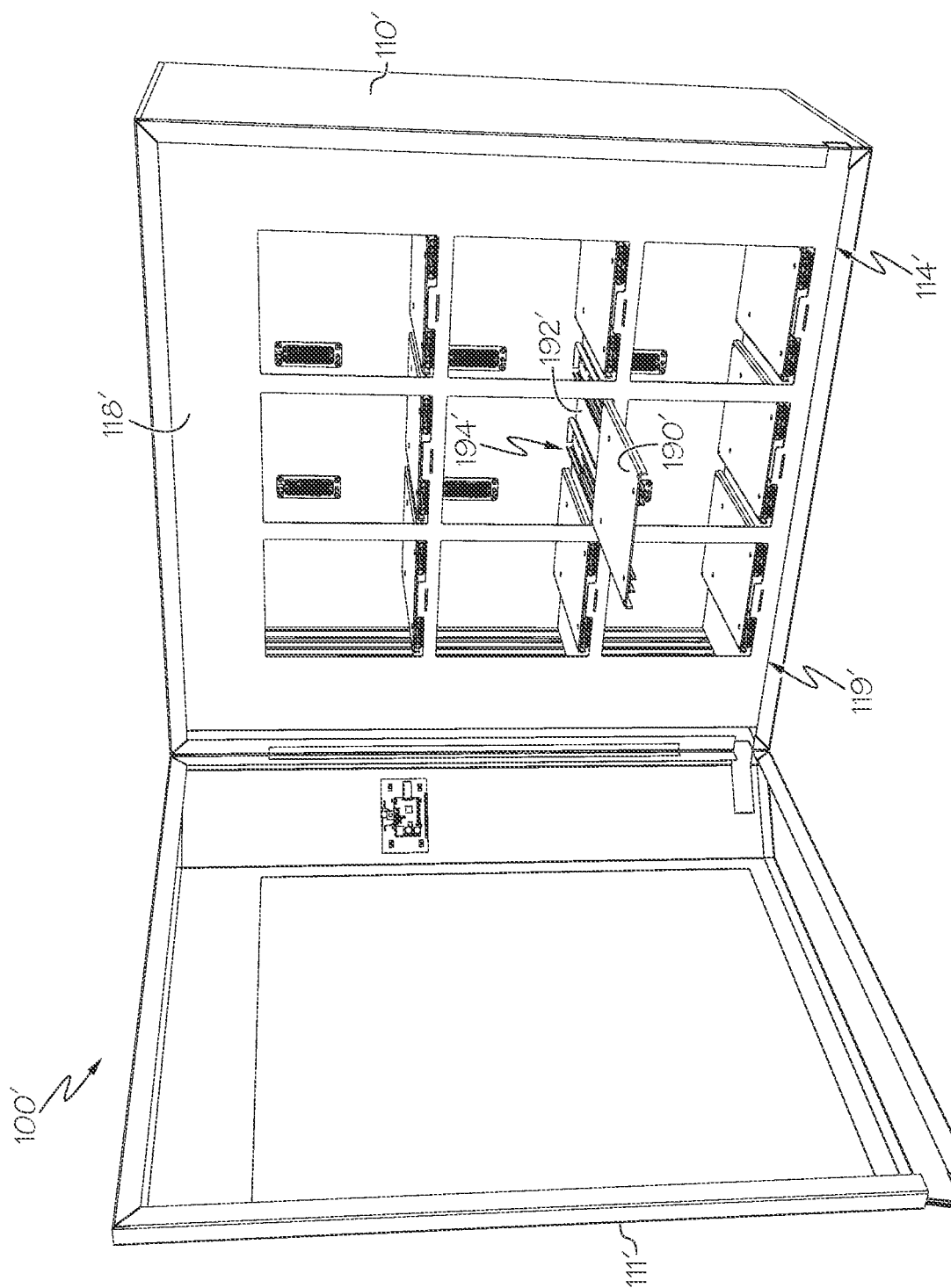
FIG. 4B depicts a perspective view of the storage assembly of FIG. 4A empty of the array of modular storage units, according to one or more embodiments shown and described herein.
Figure 4C:
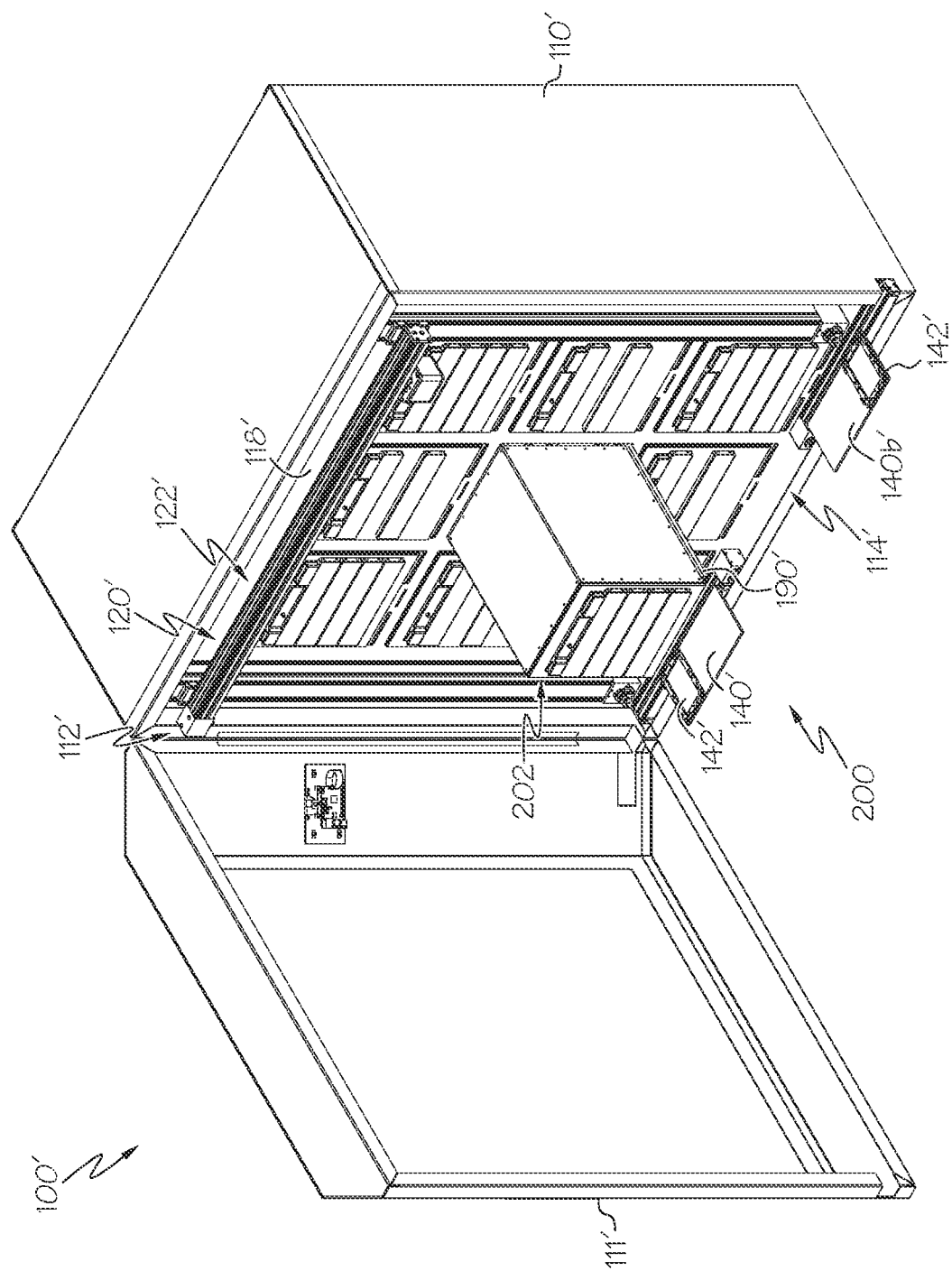
FIG. 4C depicts a perspective view of a modular storage unit being inserted into the storage assembly of FIG. 4A, according to one or more embodiments shown and described herein.
Figure 5:
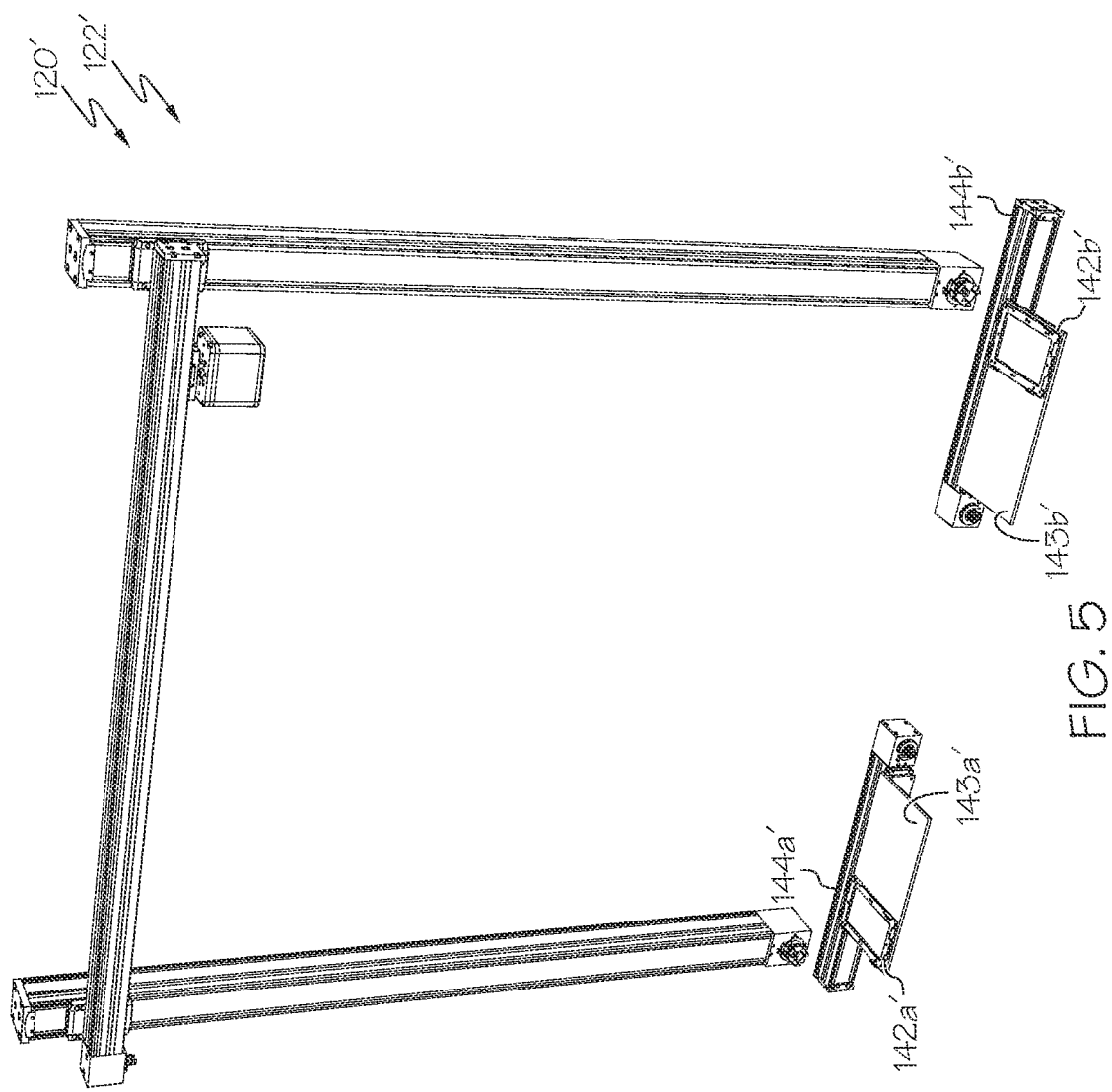
FIG. 5 depicts a sample transfer apparatus in isolation from the storage assembly of FIG. 4A, according to one or more embodiments shown and described herein.

FIGS. 4A-4C illustrate an alternative embodiment of a storage assembly 100' for storing a plurality of specimens is depicted. The embodiment is substantially similar to the storage assembly 100 except as otherwise noted or apparent from the figures. In particular, the storage assembly 100' includes a control system 101', a frame 110', a plurality of modular storage units 200 arranged in an array, and a sample transfer apparatus 120'.

In the illustrated embodiment, frame 110' further illustrates a frame access door 111' that may provide a user with access into the transfer corridor 112' and storage corridor 114' of the storage assembly 100'. As noted above, such access may allow a user to insert a modular storage unit 202 into an opening 119' of the storage compartment array 118'. Additionally, the frame access door 111', in some embodiments, may include a window through which a user may observe the contents of the storage assembly 100'. The window may be an OLED touch screen or other touch screen device, such that the user interface device is incorporated into the window of the frame access door 111'. In other embodiments and as illustrated in FIG. 4A, the user interface device 104' may be mounted to the door as a touch screen or other user interface device as described above.

Additionally, FIG. 4B illustrates the storage compartment array 118' as empty. In the illustrated embodiments, each opening 119' of the storage compartment array 118' is provided with a sliding deck 190' that is mounted to a base surface 192' of the opening by one or more rails 194' (e.g., two rails). The sliding deck 190' is slidable along the one or more rails 194' to extend the sliding deck 190' outside of the opening 119' of the storage compartment array 118'. The sliding deck 190' may be provided with one or more guide pins (not shown) that are configured to mate with one or more recesses formed on a bottom surface of the modular storage unit 202 to ensure proper placement of the modular storage unit 202 on the sliding deck 190'. As illustrated in FIG. 4C, a modular storage unit 202 may be aligned with and mounted on the sliding deck 190'. The sliding deck 190' and modular storage unit 202 may then be slid into position within the storage compartment array 118'. The sliding deck 190' may simplify insertion and removable of a modular storage unit 202.

The sample transfer apparatus 120' may be substantially similar to the sample transfer apparatus 120 and include a two dimensional gantry 122' and a conveyor 140', except in the present embodiment, the sample transfer apparatus 120' may include a first conveyor 140a' and a second conveyor 140b'. The first conveyor 140a' may be configured to convey a first delivery platen 142a' out of the first entry/egress port 115a' and the second conveyor 140b' may be configured to convey a second delivery platen 142b' out of the second entry/egress port 115b'. For example, each conveyor 140a', 140b' may include a short linear guide rail 144a', 144b'. The delivery platen 142a', 142b' may be mounted to a plate 143a', 143b' that is slidably engaged with the linear guide rail 144a', 144b'. Each conveyor 140a', 140b' may further include a separately controllable actuator (not shown) to facilitate motion of the first and second delivery platens 144a', 144b' out of their respective entry/egress ports 115a', 115b'. In such embodiments, improved efficiency in transfer of specimen holders into and out of the storage assembly 100' may be recognized, as two specimen holders may be moved into and/or out of the storage assembly 100' simultaneously and/or independently.

FIGS. 6A-6G depict a method of storing a specimen holder 10 into a desired modular storage unit 202. It is noted that while the following description refers to the storage assembly 100 described above, the method would be identical or near identical in regards to storage assembly 100' unless otherwise noted or apparent from the above description.

Figure 6A:
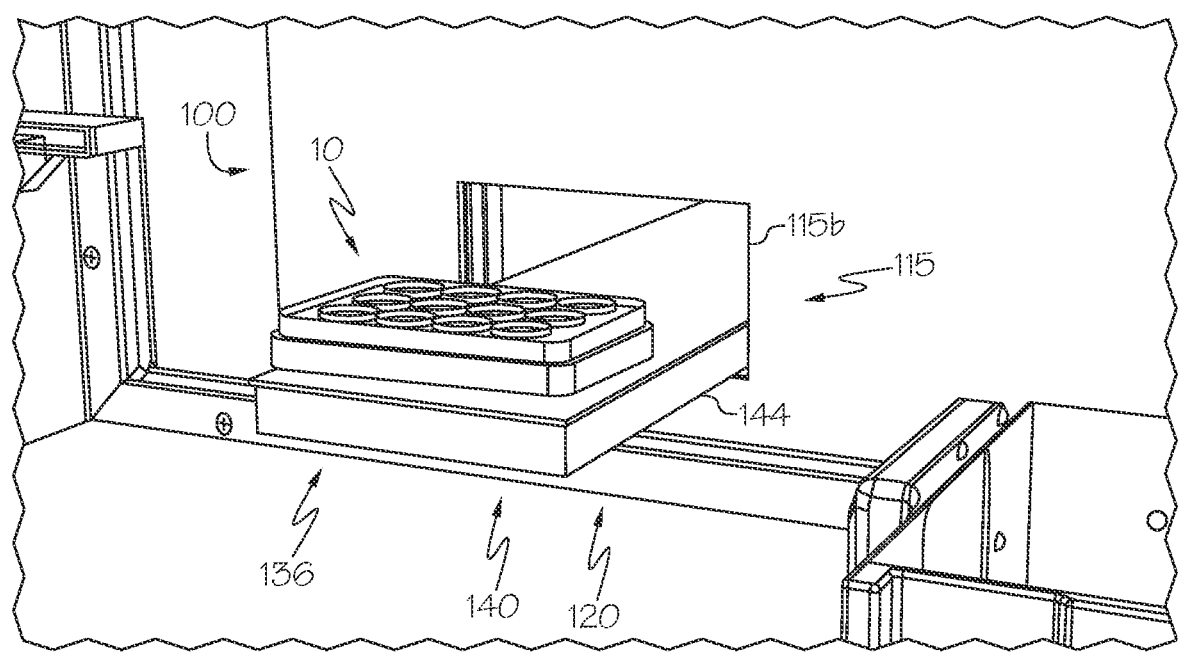
FIG. 6A depicts a specimen holder being transferred from a position outside of the storage assembly with a sample transfer apparatus, according to one or more embodiments shown and described herein.
Figure 6B:
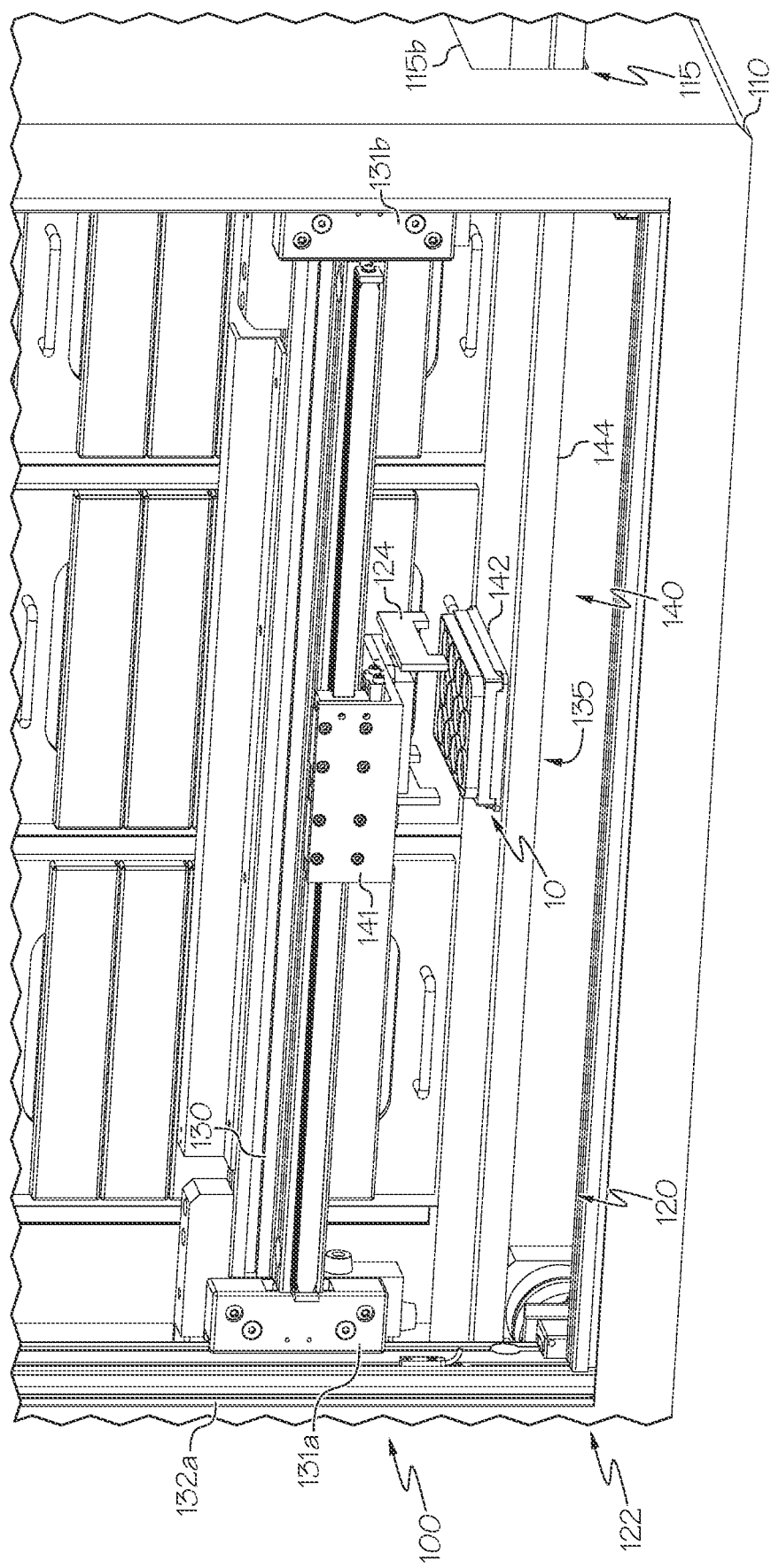
FIG. 6B depicts the specimen holder being transferred by the sample transfer apparatus to a platen home position, according to one or more embodiments shown and described herein.
Figure 6C:
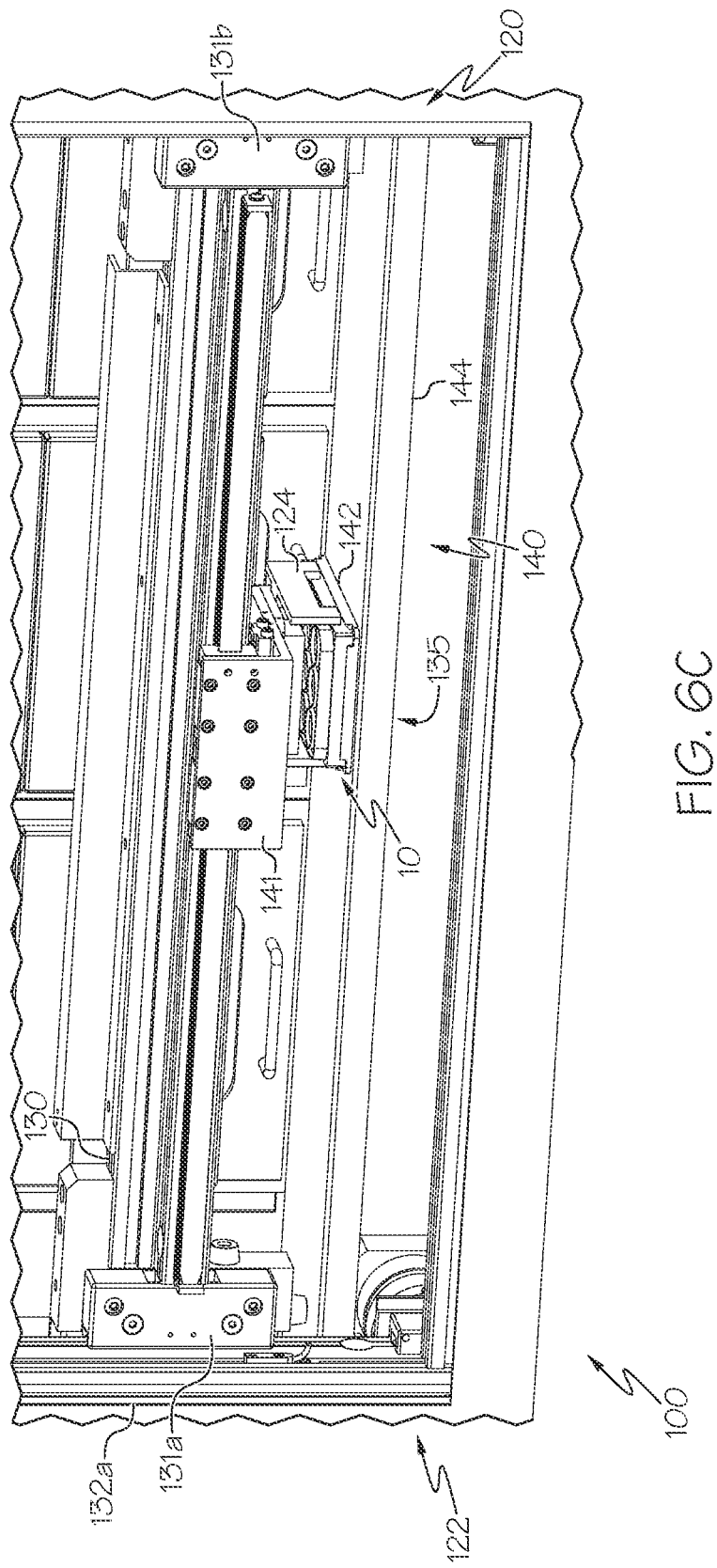
FIG. 6C depicts a gripping device gripping the specimen holder, according to one or more embodiments shown and described herein.
Figure 6D:
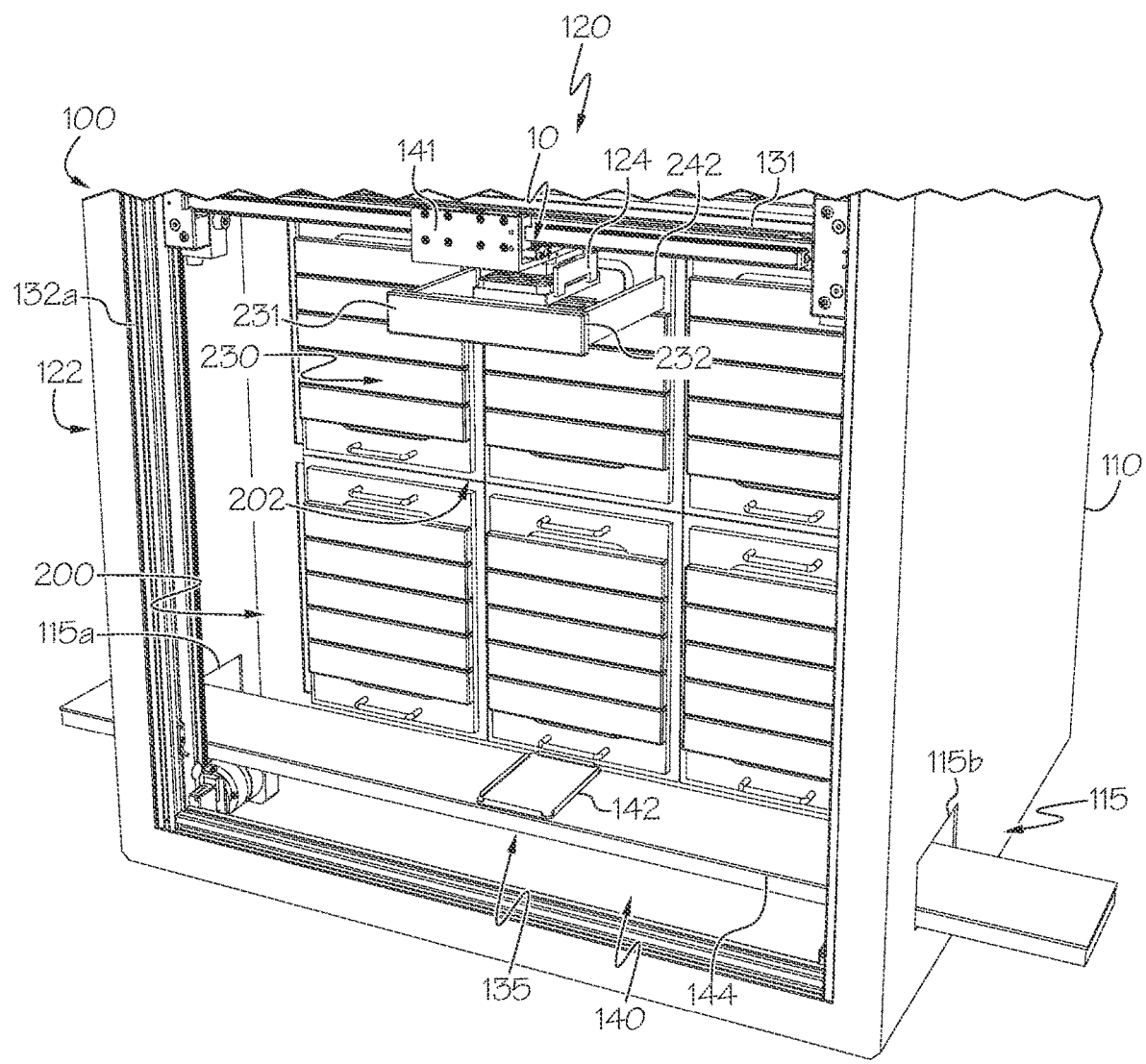
FIG. 6D depicts the gripping device lifting the specimen holder to a position above a drawer of a modular storage unit and the drawer moving to an open position, according to one or more embodiments shown and described herein.
Figure 6E:
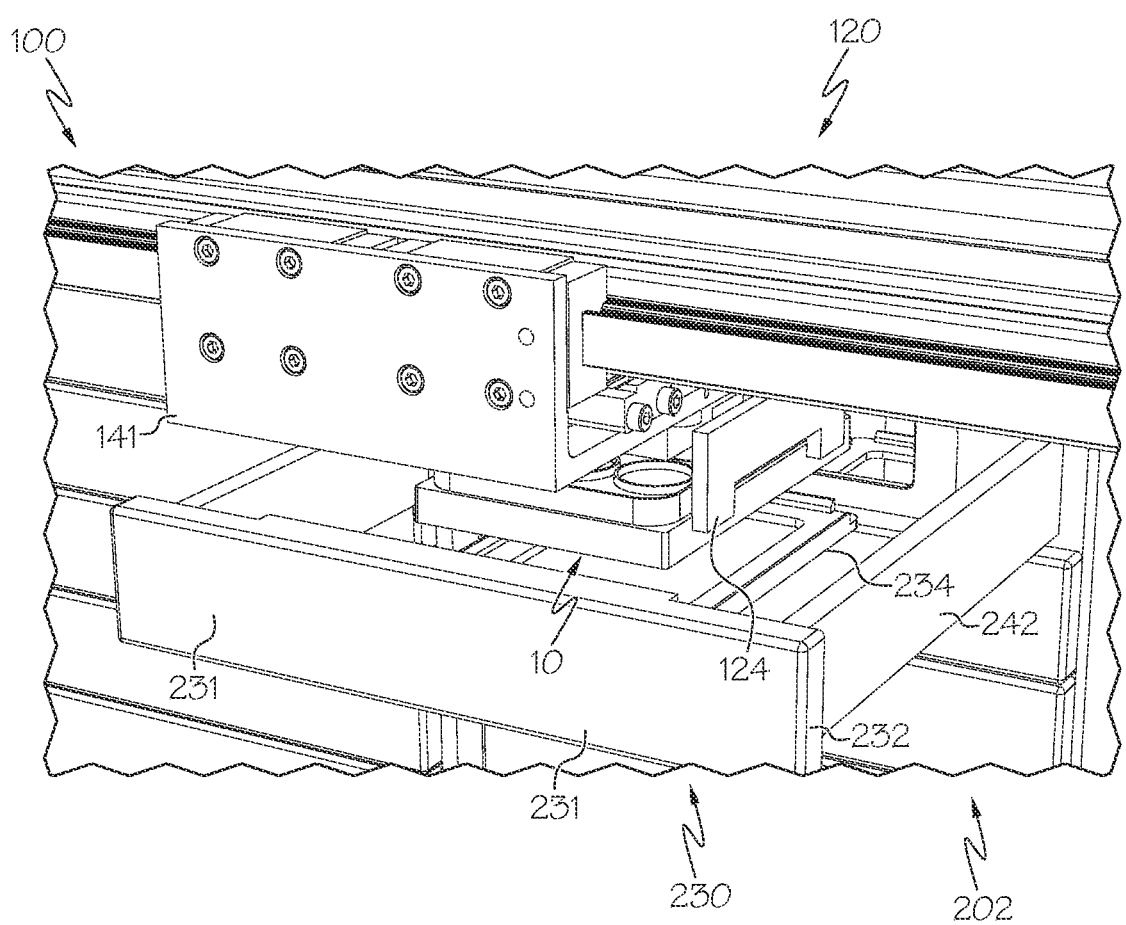
FIG. 6E illustrates the gripping device being lowered into the drawer to move the specimen holder toward a specimen support surface within the drawer, according to one or more embodiments shown and described herein.
Figure 6F:
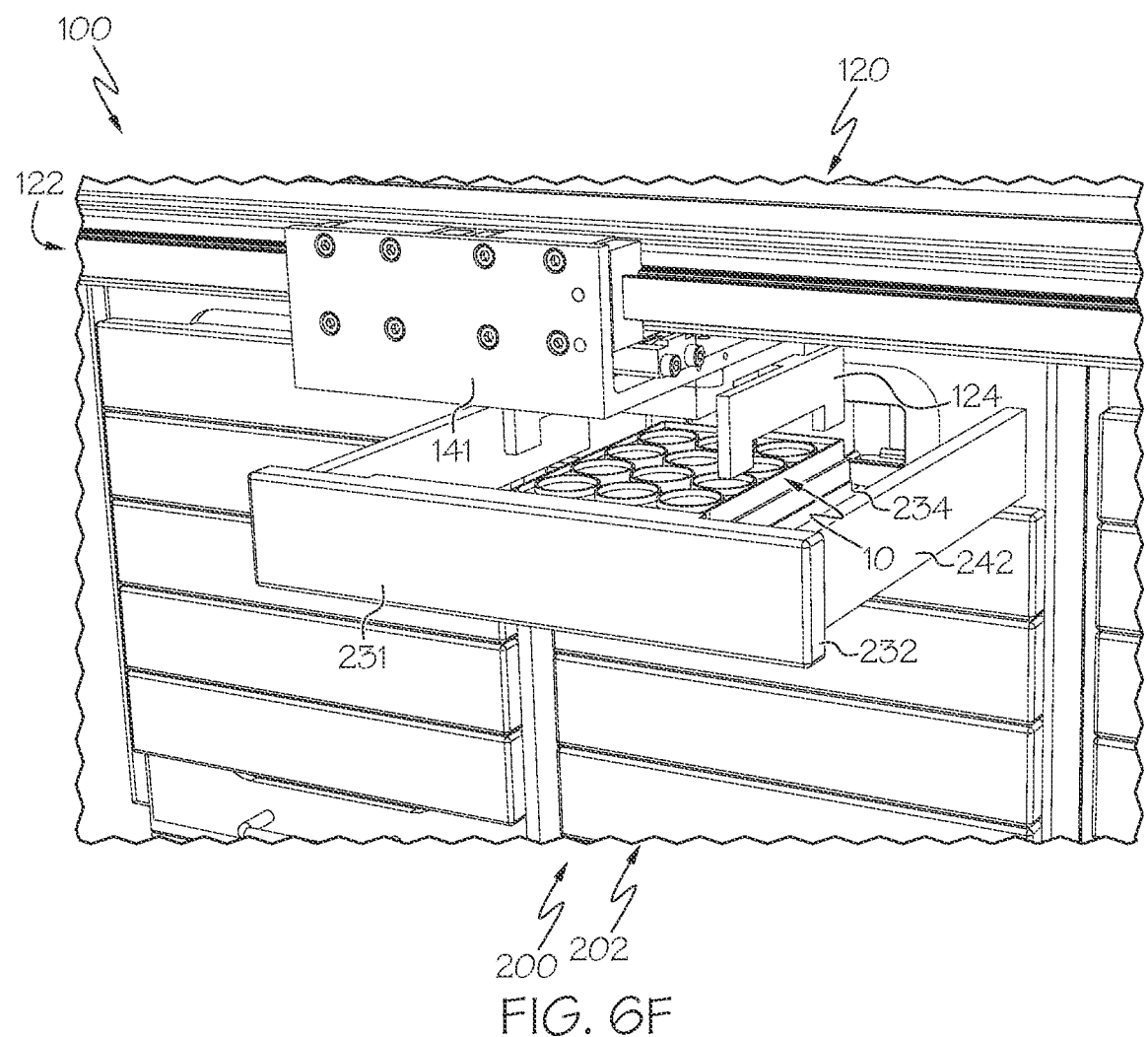
FIG. 6F illustrates the gripping device releasing the specimen holder within the drawer and raising to a position which provides clearance for the drawer to close, according to one or more embodiments shown and described herein.
Figure 6G:
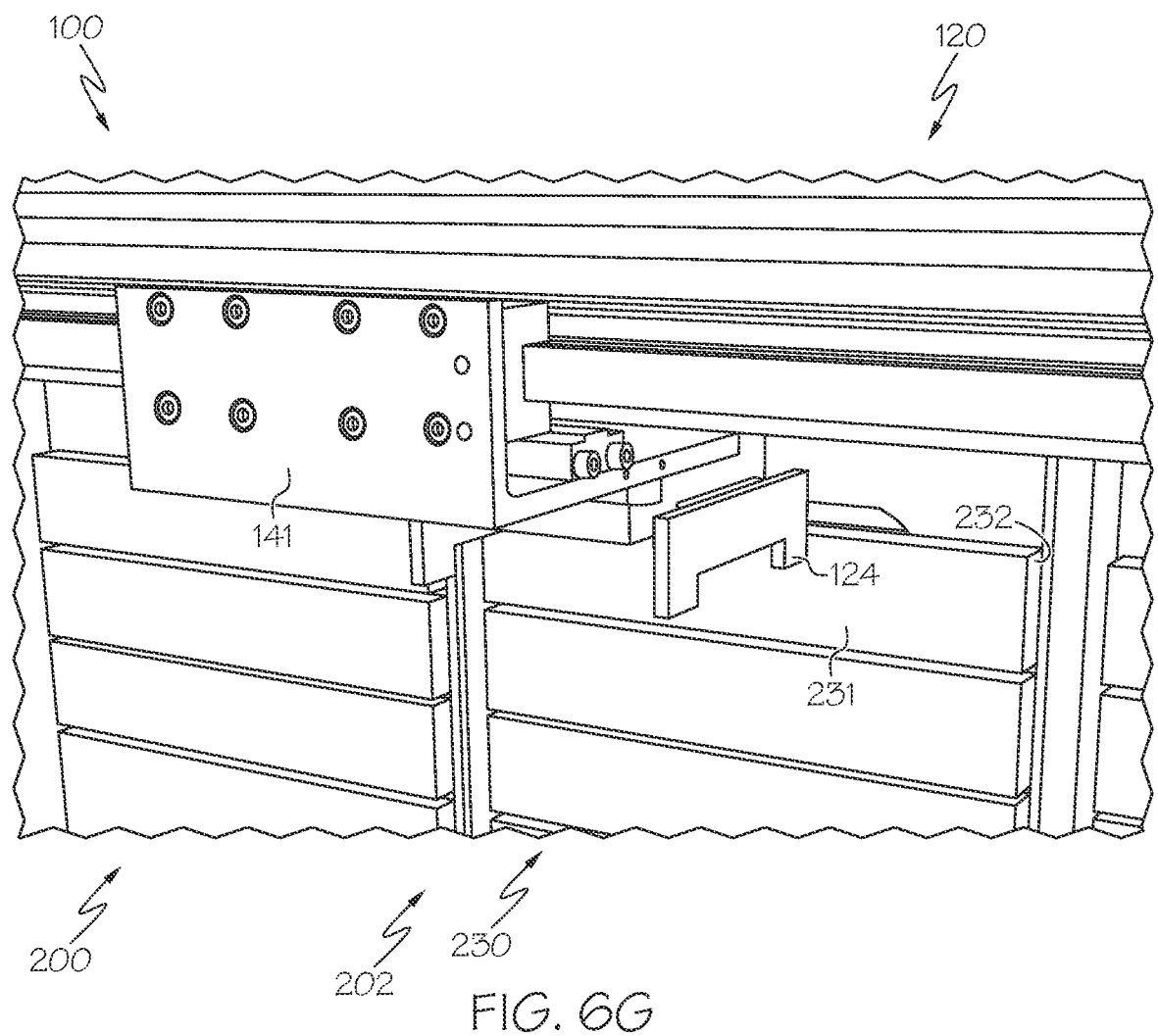
FIG. 6G illustrates the drawer in a closed position, according to one or more embodiments shown and described herein.
Figure 7A:
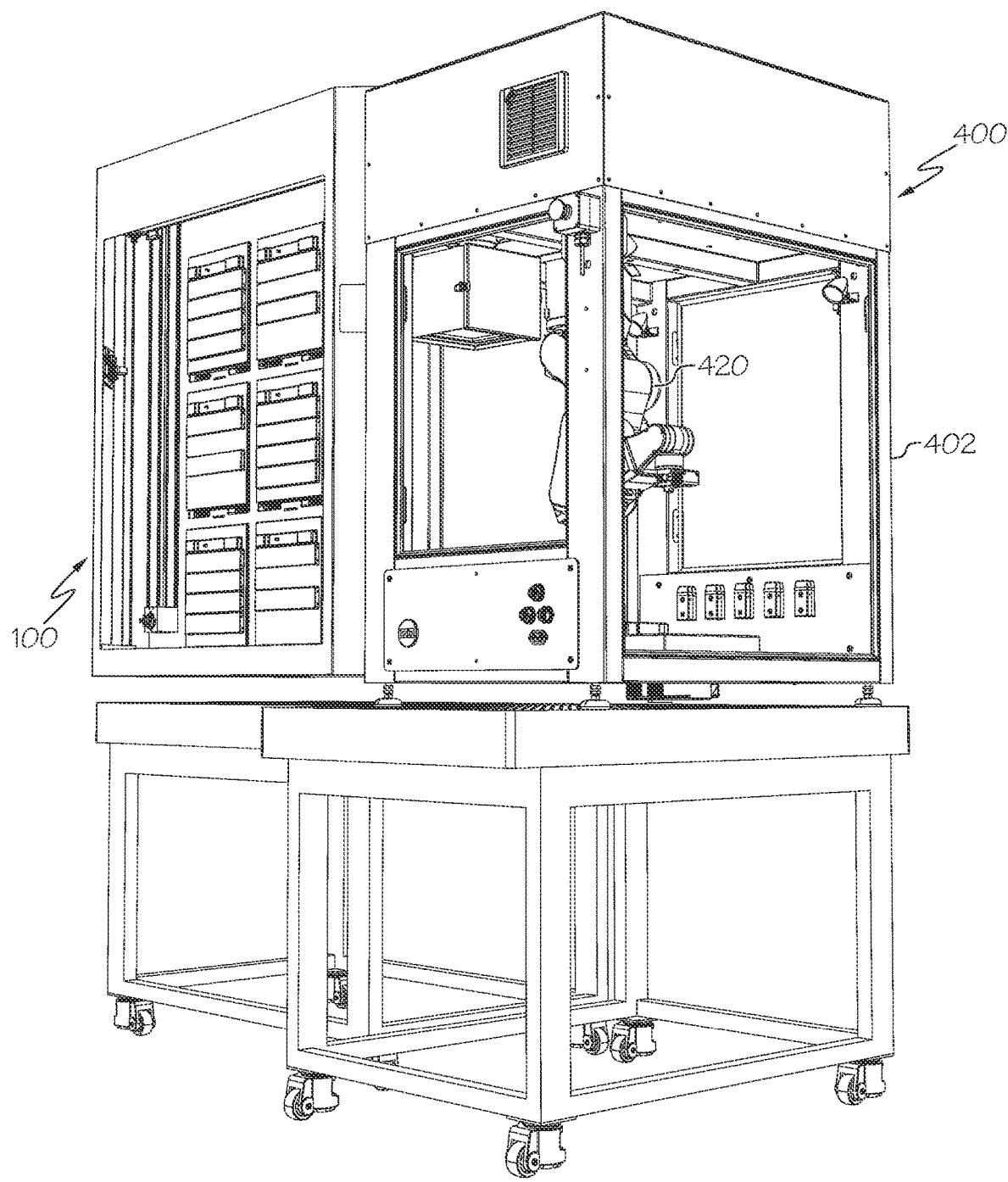
FIG. 7A illustrates a storage assembly mounted relative to a biologic printing stage, according to one or more embodiments shown and described herein.
Figure 7B:
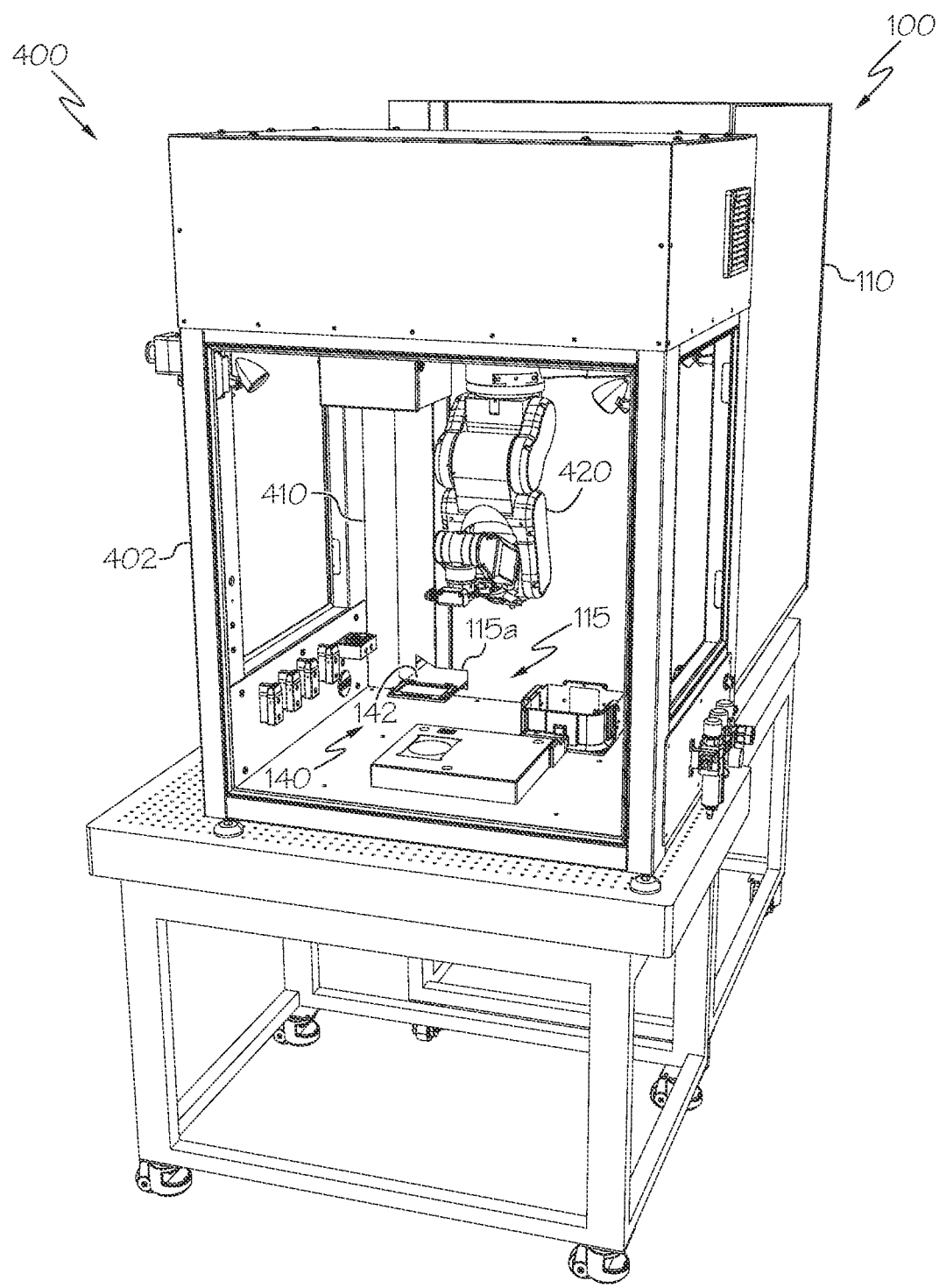
FIG. 7B illustrates a conveyor of a sample transfer apparatus of the storage assembly of FIG. 7A positioned within the biologic printing assembly, according to one or more embodiments shown and described herein.

Storage of a specimen within a modular storage unit 202 may be prompted by a user requesting, using the user interface device 104, storage of the specimen and/or specimen holder 10. However, in some embodiments, storage of a specimen may be automatic based on pre-programmed incubation and/or perfusion instructions or protocol. In embodiments, the user may, using the user interface device 104, select a specific drawer 231 of a modular storage unit of the plurality of modular storage units 200 into which the specimen holder is to be positioned. In some embodiments, a user may manually place a specimen holder 10 on the delivery platen 142. However, in other embodiments, the specimen holder 10 may be placed on the delivery platen 142 may a robot. For example, as illustrated in FIGS. 7A and 7B, the storage assembly 100 may be mounted beside a 3D biological printing platform 400 (e.g., a 3D biological printing platform such as BioAssemblyBot® 3-D printing and robotics systems, as described in U.S. patent application Ser. No. 15/726,617, filed Oct. 6, 2017, entitled "System and Method for a Quick-Change Material Turret in a Robotic Fabrication and Assembly Platform," hereby incorporated by reference in its entirety and as available from Advanced Solutions Life Sciences, LLC of Louisville, Ky.) such that a portion of the conveyor 140 may extend into the 3D biological printing platform 400 to allow for motion of the delivery platen 142 into the 3D biological printing platform 400. For example, a side wall 410 of the housing 402 of the 3D biological printing platform 400 may define a port or other opening into the housing 402 to allow for transfer of a specimen holder 10 into or out of the 3D biological printing platform 400. The 3D biological printing platform 400 may use a robotic arm 420 having a pick and place tool (not shown) coupled thereto to move the specimen holder 10 onto an awaiting delivery platen 142. Once in place, the control unit 102 may cause the conveyor 140 to withdraw the delivery platen 142 into the frame 110 of the storage assembly 100 to a platen home position 135, as illustrate in FIG. 6B. A standard or known home position may allow the gripping device 124 described above to predictably and repeatably locate and retrieve a specimen holder 10, as illustrated in FIGS. 6B and 6C. Referring to FIG. 6D, the gripping device 124 may then be moved by the two-dimensional gantry 122 to a desired position. In the illustrated embodiment, each modular storage unit 202 may have one or more automated drawer assemblies 230 which may be controlled by the control unit 102 to automatically open to receive the specimen holder 10 (or for retrieval of the specimen holder 10 therefrom). As illustrated in FIG. 6D-6F, the gripping device 124 may position the specimen holder 10 within a designated drawer of the modular storage unit 202 and release the specimen holder 10 into the designated drawer 231. After releasing the specimen holder 10, the gripping device 124 may be lifted to a position above the drawer such that the drawer may be drawn closed by to control unit 102.

Similarly, to retrieve a specimen holder 10 (per user instructions or per automation), the gripping device 124 would similarly be placed so as to hover above a desired drawer 231, the drawer 231 would be automatically opened by the control unit 102. The gripping device 124 may be placed into the drawer and closed around the specimen holder 10. The gripping device 124 may then be raised with the specimen holder 10 out of the way of the drawer 231, such that the drawer 231 may be automatically closed by the control unit 102. The gripping device 124 may then be moved to the platen home position 135 and release the specimen holder 10 onto the delivery platen 142, which may then be delivered outside the storage assembly 100 by the conveyor 140 to a known delivery position 136. For example, the conveyor 140 may always cause the delivery platen 142 to move to the same delivery position 136. Such may allow the robotic arm 420 of the 3D printing platform 400 to pick up the specimen holder 10 from or place the specimen holder 10 correctly on the delivery platen 142 in a predictable and repeatable manner.

In some embodiments, instead of delivering the specimen holder 10 to the conveyor 140, the specimen holder 10 may be delivered to a different modular storage unit 202 having, for example, a different incubation environment and/or perfusion environment. For example, the user interface device 104 may allow a user to input or select an automated robotic workflow protocol wherein the control unit 102 automatically moves the specimen holder 10 into and/or out of different modular storage units 200 for prescribed times. For example, a user may generate a specimen workflow with the user interface device 104 that would place a specimen in a first modular storage unit under normoxic conditions for, e.g., 7 days, then programmatically the specimen via the sample transfer apparatus 120 to a second modular storage unit within the storage assembly 100 and hold the specimen under hypoxic conditions for, e.g., 3 days. Such iterative workflow may possible when a multitude of independently controlled modular storage units 200 are readily available and programmatically set for a variety of incubation and/or perfusion conditions.

As noted above, the plurality of modular storage units 200 may be configured for incubation and/or perfusion applications. The various components of a modular storage unit 202 may be interchangeable such that any of the modular storage units 200 may become an incubation storage unit, a perfusion storage unit, or a combination thereof.

Figure 8B:
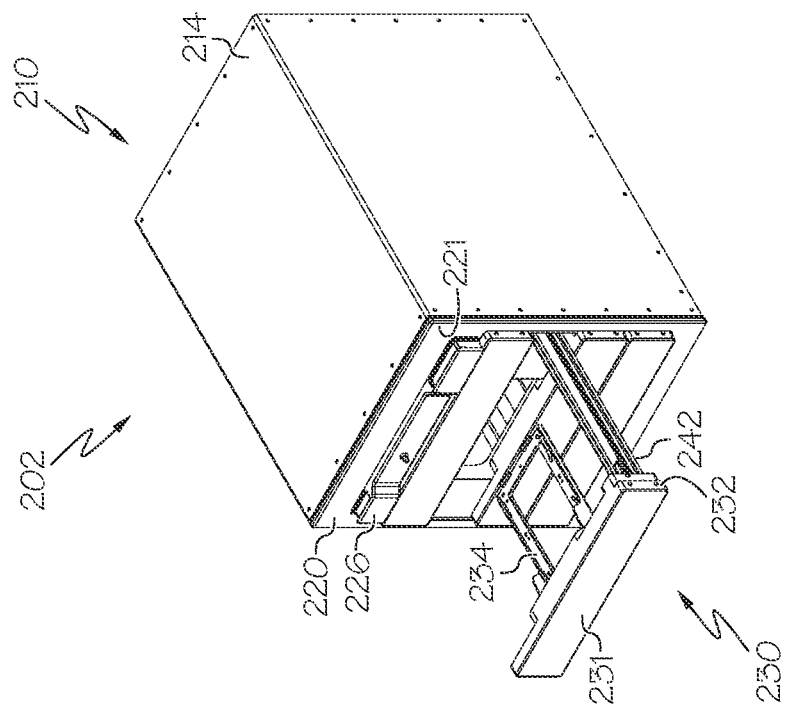
FIG. 8B illustrates the modular storage unit of FIG. 8A with an open drawer, according to one or more embodiments shown and described herein.
Figure 8A:
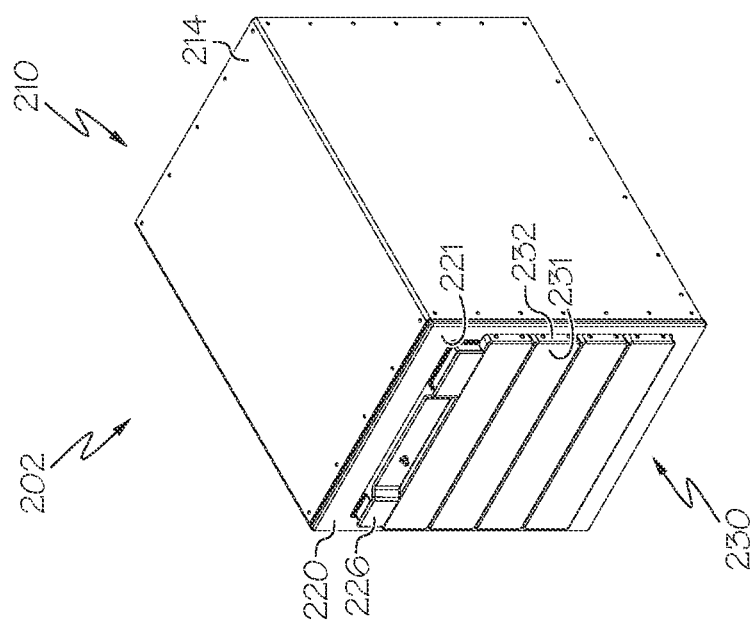
FIG. 8A illustrates a perspective view of a modular storage unit assembled for incubation applications, according to one or more embodiments shown and described herein.
Figure 8C:
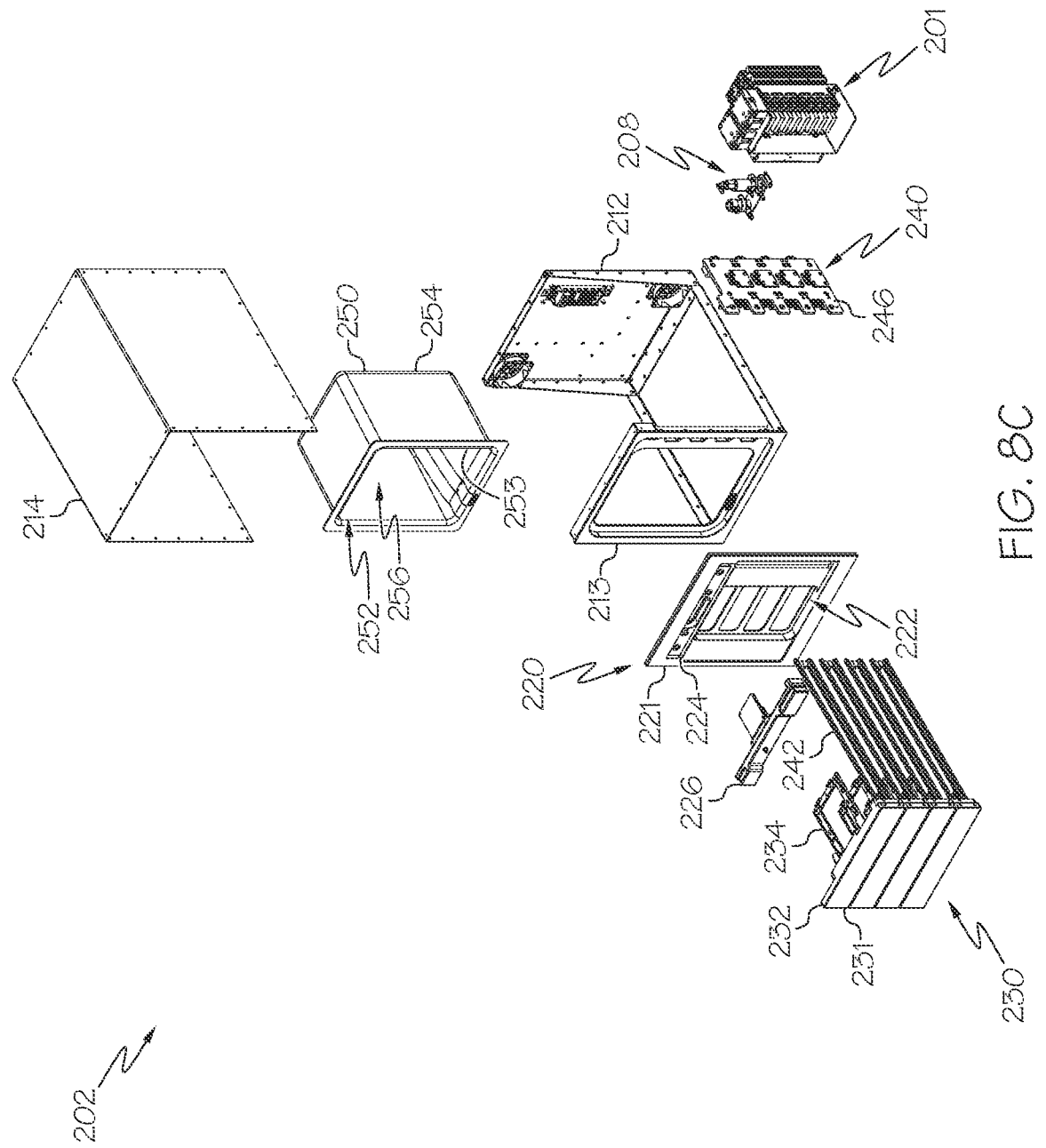
FIG. 8C illustrates an exploded view of the modular storage unit of FIG. 8A, according to one or more embodiments shown and described herein.
Figure 8D:
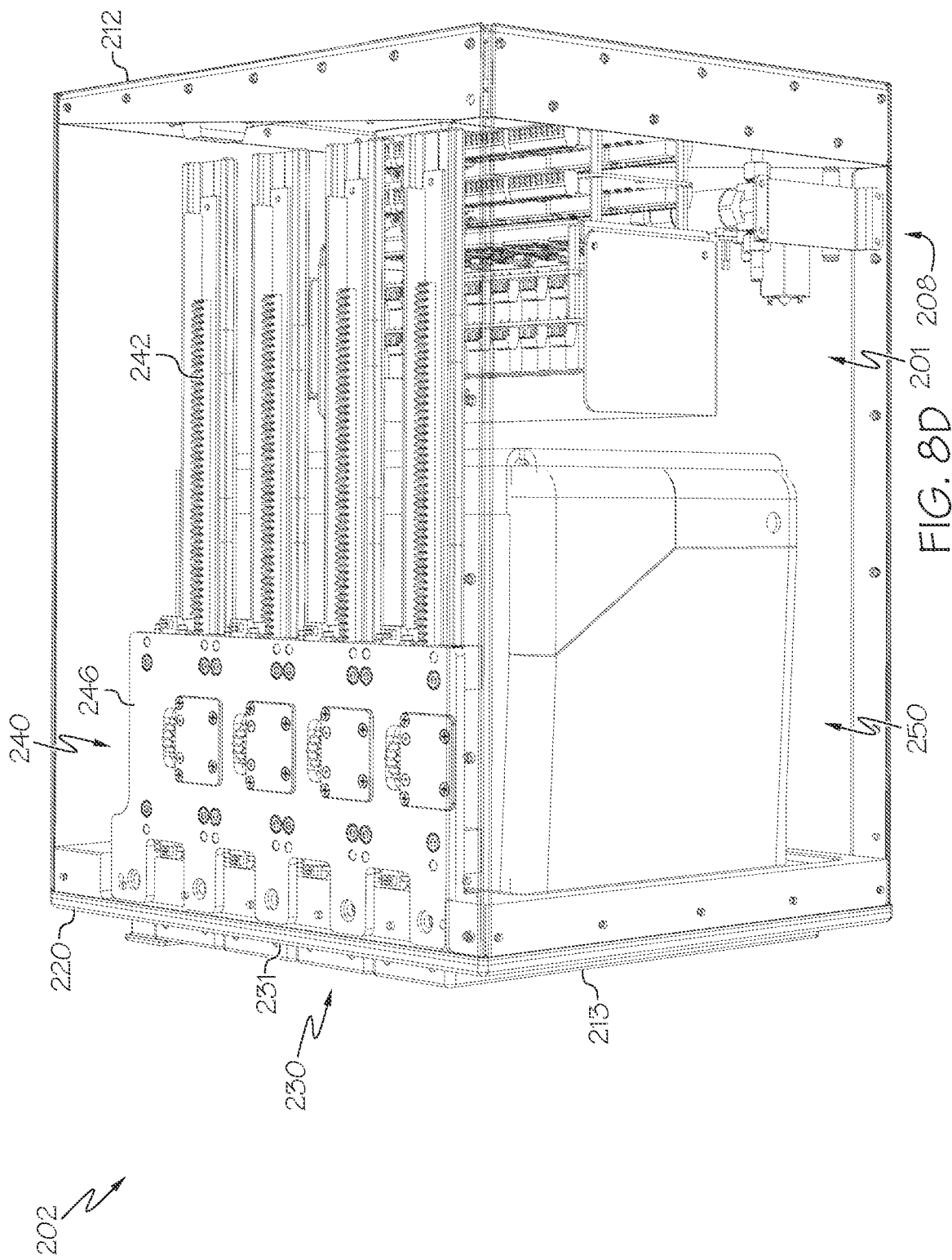
FIG. 8D a partial view of an assembled interior of a modular storage unit, according to one or more embodiments shown and described herein.
Figure 9B:
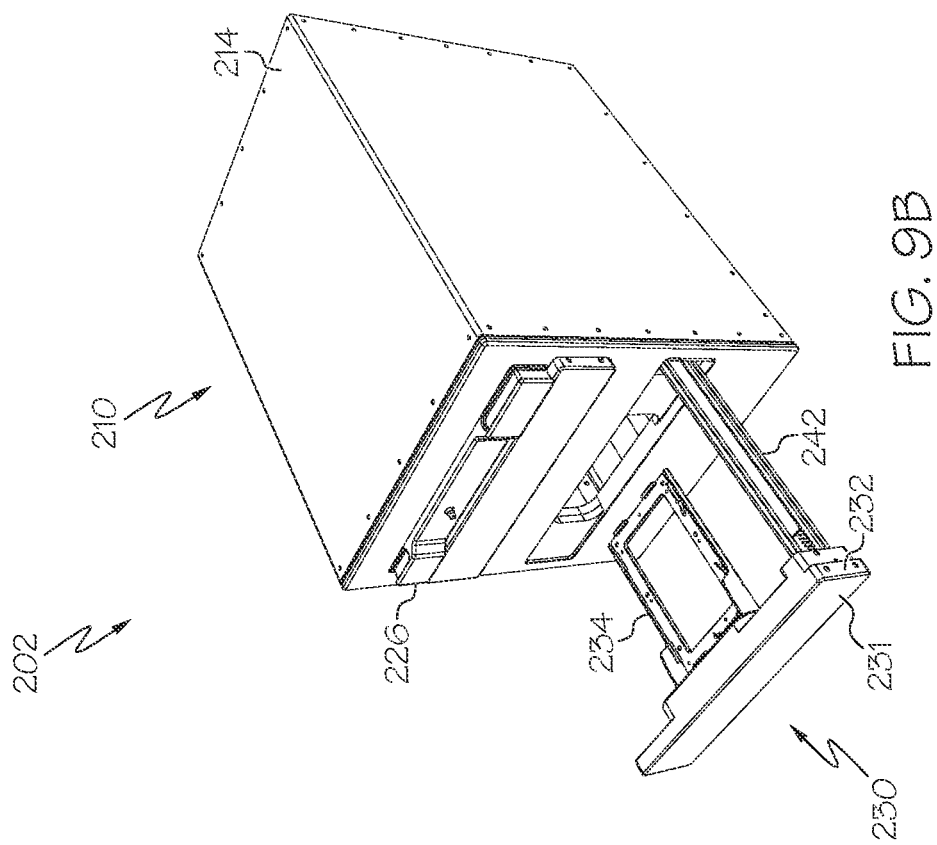
FIG. 9B illustrates the modular storage unit of FIG. 9A with an open drawer, according to one or more embodiments shown and described herein.
Figure 9A:
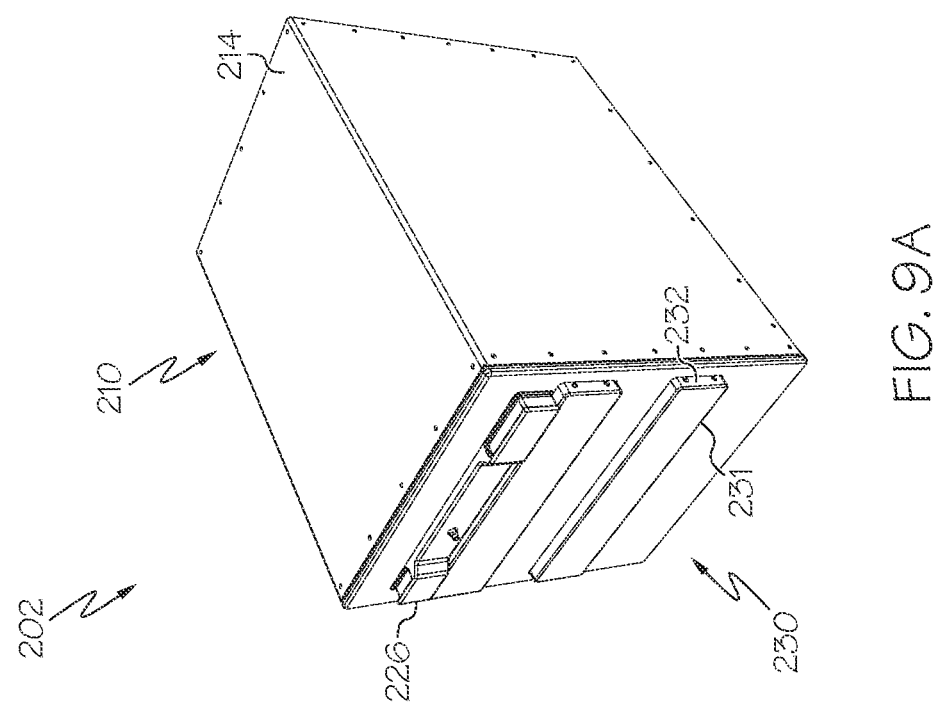
FIG. 9A illustrates a perspective view of a modular storage unit assembled for perfusion applications, according to one or more embodiments shown and described herein.
Figure 9C:
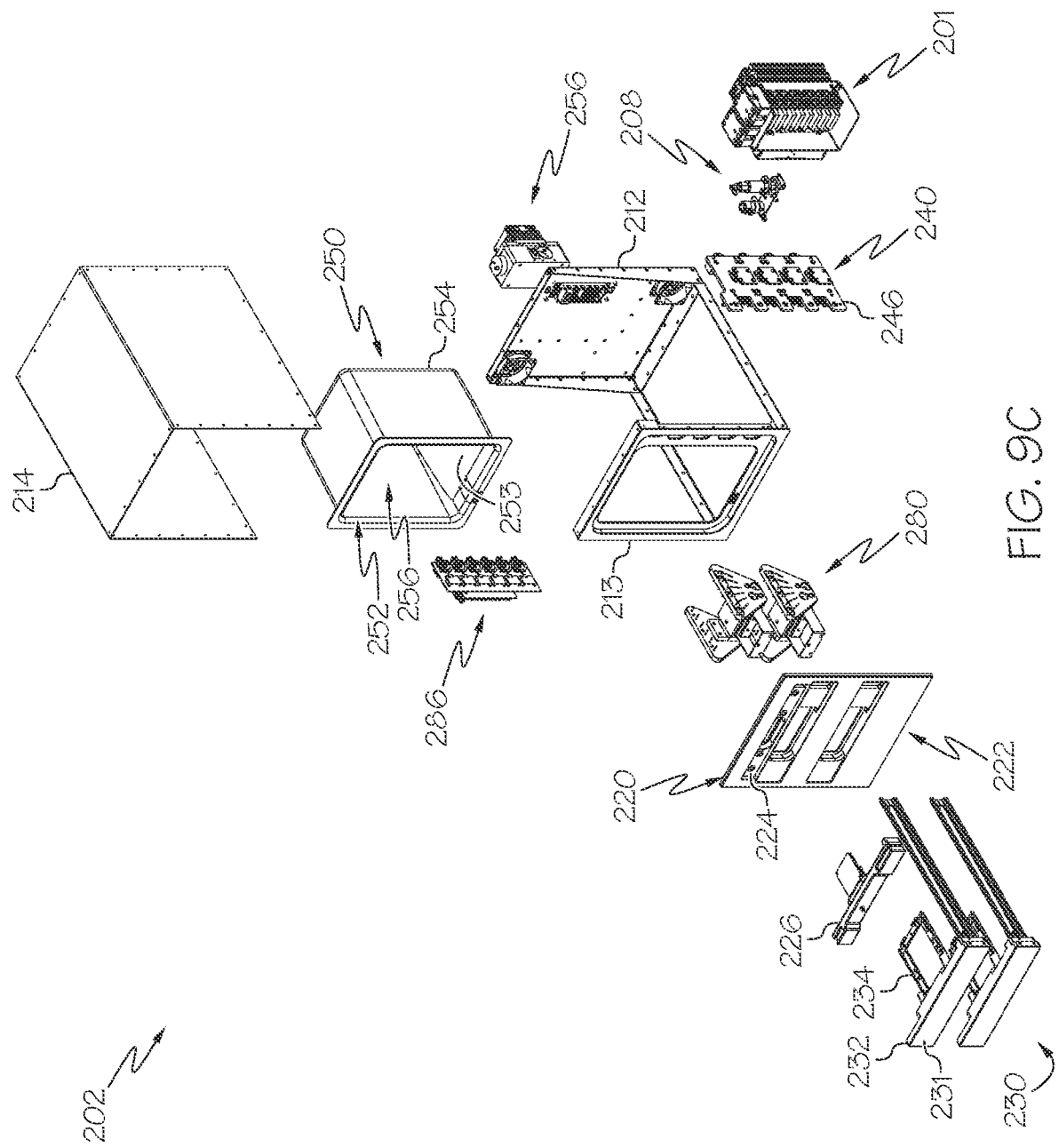
FIG. 9C illustrates an exploded view of the modular storage unit of the 9A, according to one or more embodiments shown and described herein.

FIGS. 8A and 8B illustrate an exterior view of a modular storage unit 202 and FIG. 8C illustrates an exploded view of the modular storage unit 202 to illustrate various interior components that may be incorporated within the modular storage unit 202 when the modular storage unit 202 is assembled as an incubation unit. FIG. 8D illustrates a partial interior view of the modular storage unit 202. FIGS. 9A-9C illustrate the modular storage unit 202 assembled as a perfusion unit. Accordingly, unless otherwise noted, incubation units and perfusion units have identical or near identical components. In general, the modular storage unit 202 generally includes an enclosure 210 and an automated drawer assembly include a replaceable faceplate 220 and one or more drawers 231.

The enclosure 210 may generally define the outer casing of the modular storage unit 202. Referring to FIGS. 8C and 9C the enclosure 210 may include an enclosure frame 212 and an enclosure cover 214 that is couplable to the enclosure frame 212 to form an enclosed space within the enclosure to receive one or more drawers. The enclosure frame 212 may define a faceplate interface 213 onto which the replaceable faceplate 220 may be mounted. For example, the replaceable faceplate 220 may mount to the faceplate interface 213 of the enclosure frame 212 via magnets, fasteners, or the like. In embodiments where the replaceable faceplate 220 is magnetically coupled to the enclosure frame 212, the magnetic coupling may provide faster and/or easier movement and/or replacement of the replaceable faceplate 220 and/or service access to the modular storage unit 202.

The replaceable faceplate 220 of the automated drawer assembly 230 may define a number of drawer ports 222. The drawer ports 222 define the space in the faceplate through which a drawer 231 of the one or more automated drawer assemblies 230 of the modular storage unit 202 may be inserted. Accordingly, the number of drawer ports 222 may define the number of separate drawers 230 within a single modular storage unit 202. While the illustrated embodiment depicts four drawers, there may be a fewer or greater number of drawers depending on, for example, the size of the specimen holder 10 (e.g., larger specimens may have larger specimen holders), the size of the modular storage unit 202, and whether the modular storage unit 202 is used for perfusion purposes.

Figure 11:
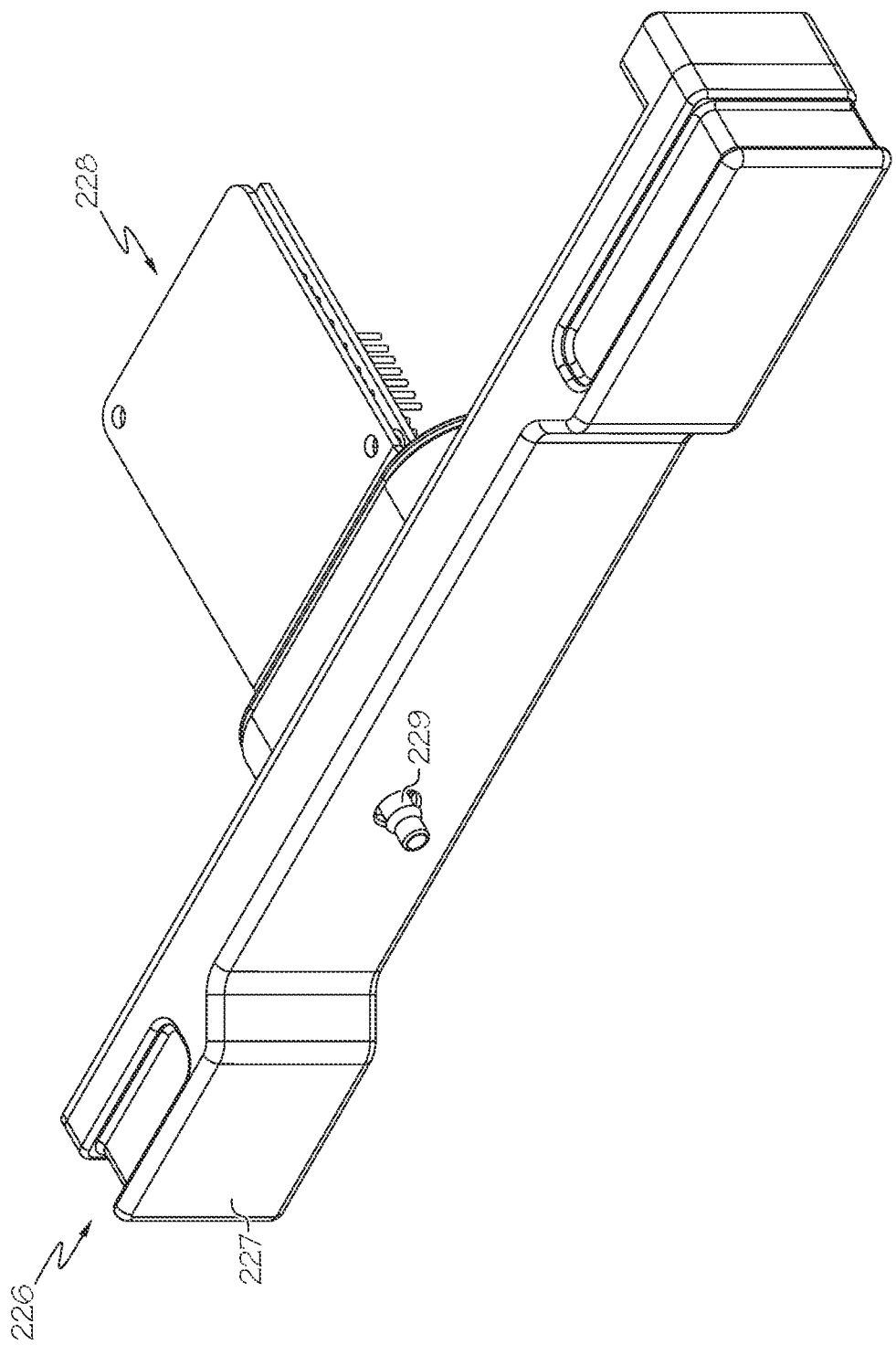
FIG. 11 depicts a sensing platform, according to one or more embodiments shown and described herein.

In some embodiments, and as illustrated in FIG. 8C, the replaceable faceplate 220 may further include a sensor port 224 for receiving a sensing platform 226. Referring to FIG. 11, the sensing platform 226 may include a platform body 227 configured to interface with the sensor port 224. The sensing platform 226 may include a plurality of sensors 228, which may be communicatively coupled to the control unit 102 via the communication path 103. For example, FIG. 11 illustrates a sensing platform 226, which may include a carbon dioxide sensor(s), a humidity sensor(s), and/or a temperature sensor(s). Feedback from the sensing platform 226 may allow the control unit 102 to ensure proper settings and make adjustments as necessary to control the environment within the modular storage unit 202. In embodiments wherein there is a carbon dioxide sensor, a carbon dioxide sampling port 229 may be provided on the platform body to allow for calibration via a calibration means such as Fyrite® or similar calibration means. In other embodiments, there may be no sensor port 224 and instead the sensors may be placed elsewhere within the enclosure 210.

Figure 12:
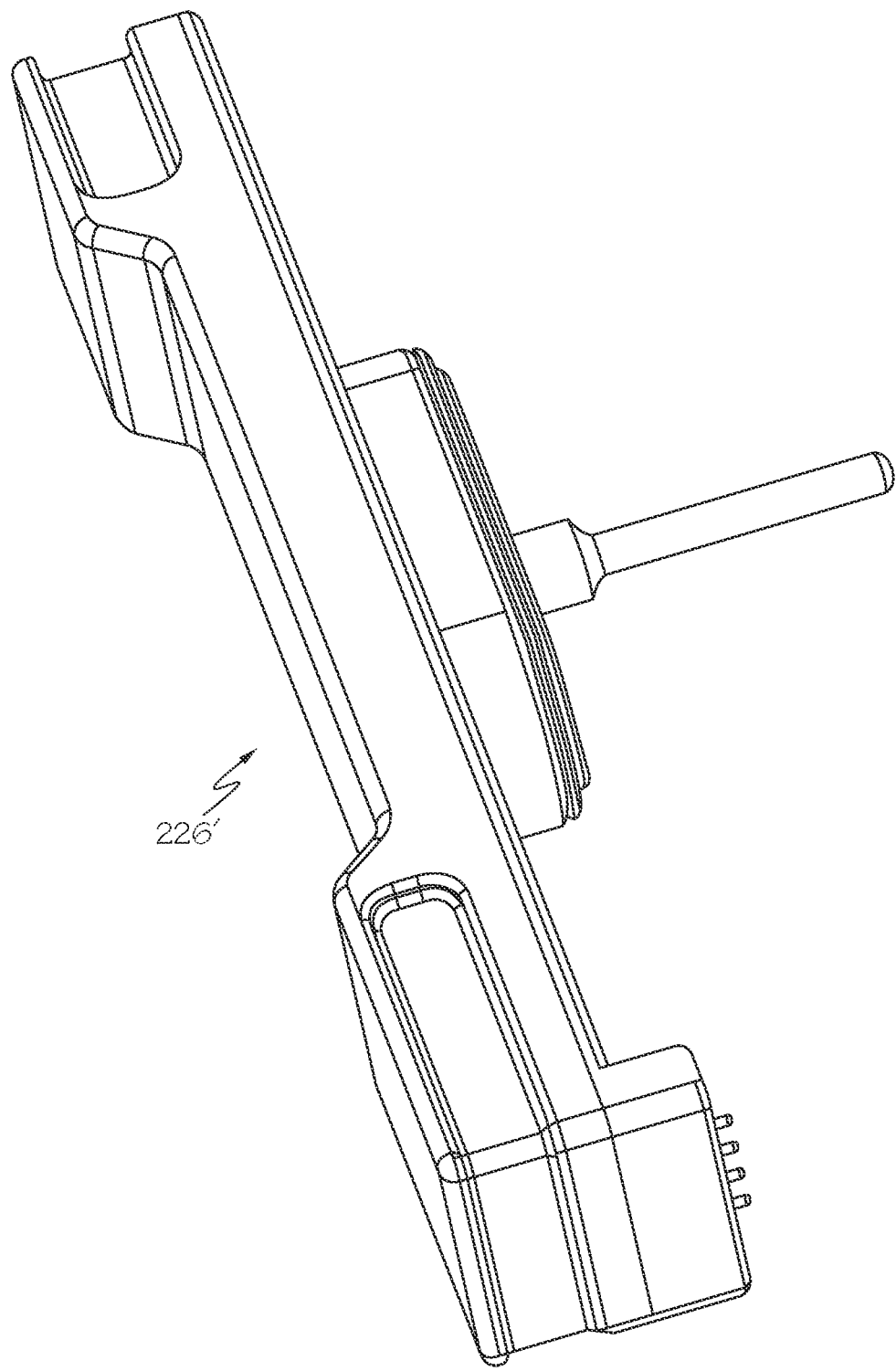
FIG. 12 depicts a sensing platform, according to one or more embodiments shown and described herein.

Sterilization of the interior of the modular storage unit 202 may sometimes be necessary. Sterilization through dry heat sterilization and/or wet heat sterilization may be used. Such sterilization procedures may be conducted at high temperatures that are not suitable for some of the above-noted sensors (e.g., carbon dioxide sensors, and/or humidity sensors.) In some embodiments, and as shown in FIG. 12 a second sensing platform 226' for sensing high temperature environments (e.g., ≥90° C.) may be used. For example, during typical incubation and/or perfusion applications that first sensing platform 226 may be inserted into the sensor port 224. However, during sterilization procedures, the first sensing platform 226 may be removed from the sensor port 224 and the second sensing platform 226' inserted, to ensure proper sterilization temperatures are reached within the modular storage unit 202.

As noted above, the one or more automated drawer assemblies 230 may include a number of drawers 231 that correspond to the number of drawer ports 222 in the replaceable faceplate 220. For example, wherein the replaceable faceplate 220 defines four drawer ports, there may be four drawers. In the illustrated embodiment, the drawers 231 may be stacked in a vertical array. However, other configurations are contemplated and possible. Each drawer 231 may include a drawer faceplate 232, a specimen support surface 234, and one or more drawer rails 242.

Figure 13A:
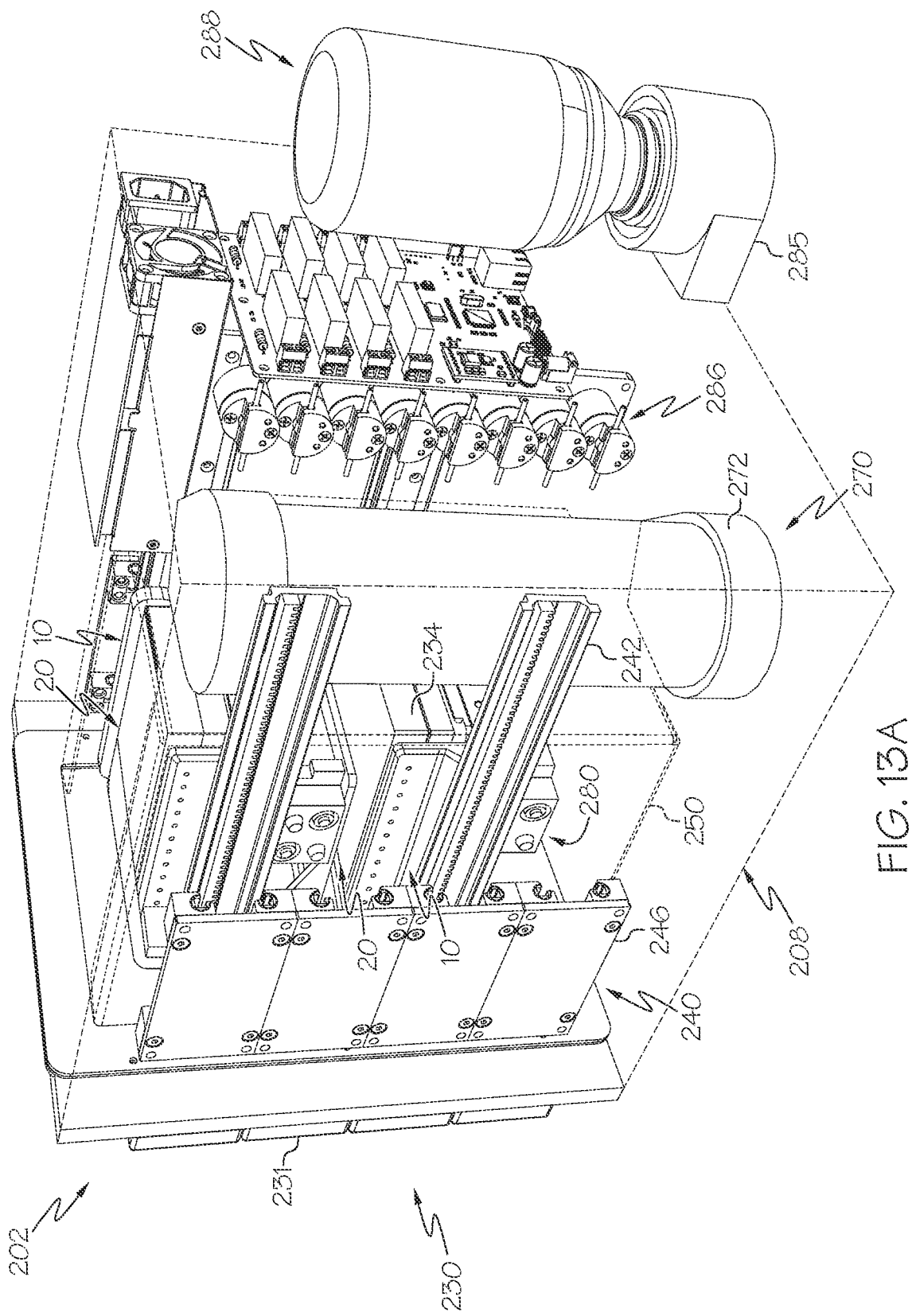
FIG. 13A depicts an interior of the modular storage unit, according to one or more embodiments shown and described herein.
Figure 13B:
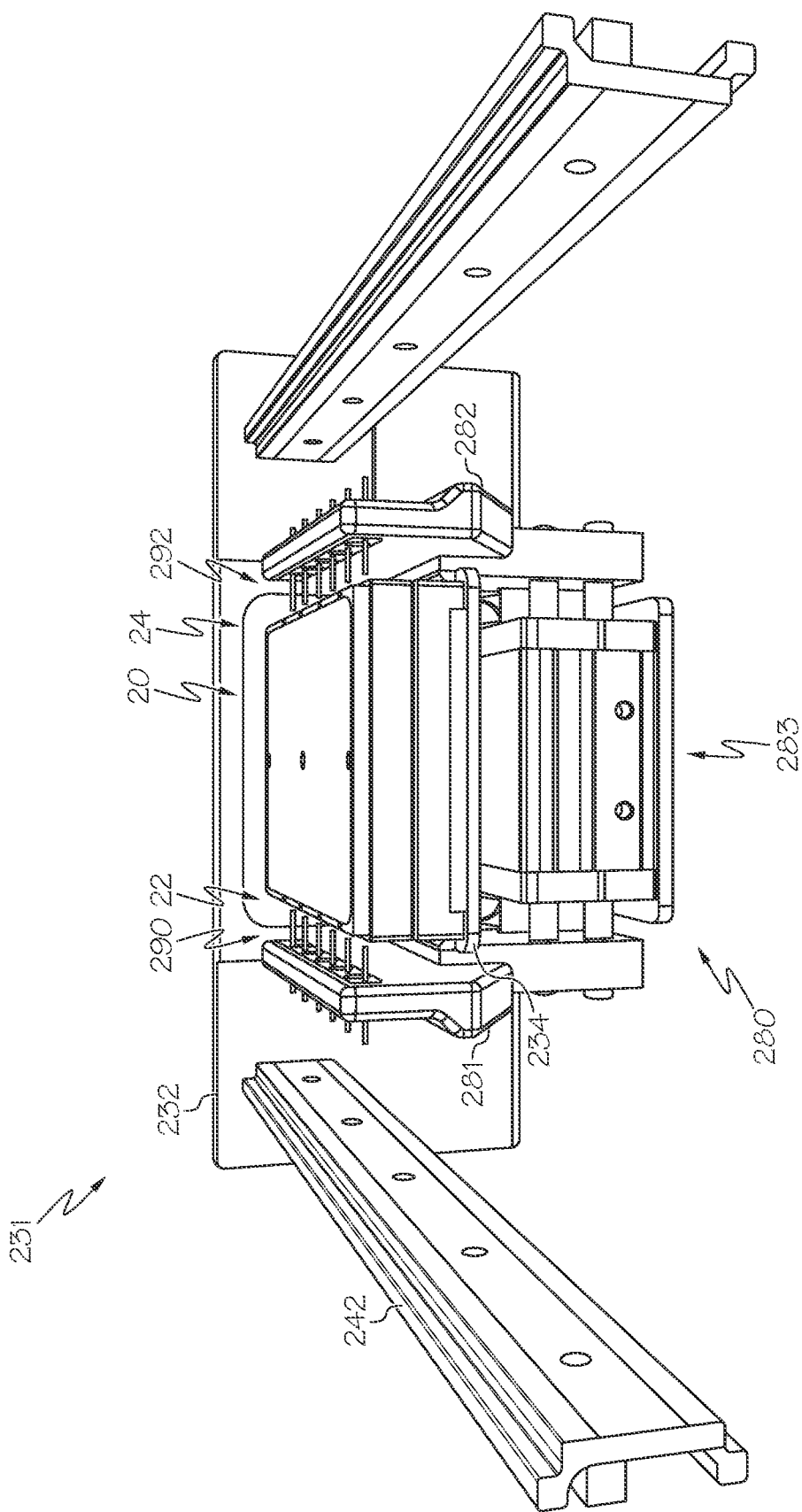
FIG. 13B illustrate a perfusion actuation apparatus of the modular storage unit of FIG. 13A in an open position, according to one or more embodiments shown and described herein.

When the drawer 231 is in a closed position, the drawer faceplate 232 may engage with an outer surface 221 of the replaceable faceplate 220. The specimen support surface 234 may be coupled to the drawer faceplate 232 and may be any shape configured to receive and support a specimen holder 10 thereon. The one or more drawer rails 242 may be coupled to either side of the specimen support surface 234 or both. For example, in the illustrated embodiment, a drawer includes only one rail 242 situated to one side of the support plate. However, in other embodiments, such as illustrated in FIGS. 13B and 13C a drawer rail 242 may be positioned on both sides of the specimen support surface 234. In either embodiment, the drawer rail 242(*s*) may be laterally spaced from the specimen holder 10 such that the specimen support surface 234 is cantilevered from the drawer faceplate 232. The one or more drawer rails 242 may facilitate automated motion into and out of the modular storage unit 202 by engaging with a motorized gearing (e.g., via a rack and pinion configuration) positioned within the modular storage unit 202.

The motorized gearing 240 may be mounted within the modular storage unit 202 to, for example, the faceplate interface 213 as illustrated in FIG. 8D, or a bottom surface 253 of the enclosure frame 212. The motorized gearing 240 may define a vertical array of drawer/gear interfaces 246. Each of which is configured to receive a drawer rail 242. Each of the drawer/gear interfaces may include a separately controllable drawer/gear interface 246 that is communicatively coupled to the control unit 102, such that the control unit 102 may independently operate each drawer to close and/or open each drawer independently of one another. In embodiments where the drawer has two drawer rails, the modular storage unit 202 may include a second motorized gearing on the opposite side to engage the second drawer rail.

Referring again to FIGS. 8C, 8D, and 9C, positioned within the enclosure 210 may be an incubation liner 250 may form part of an environmental control assembly 208 of the modular storage unit 202. The environmental control assembly 208 may include any devices, such as those described herein, that are used to adjust or control an environment with the modular storage unit 202. It is noted that the environmental control assembly may also include tubing, pumps, valves, sensors (e.g., flow and/or pressure sensors), etc. positioned interior and/or exterior of the modular storage unit 202.

The incubation liner 250 may be insulated and or heated for controlling a temperature within the modular storage unit 202. For example, the incubation liner 250 may include resistive heating coils that heat the liner, although other heating means are contemplated and possible. The control unit 102 may be communicatively coupled to the incubation liner 250 to control the temperature of the interior of the modular storage unit 202 with the incubation liner 250. As illustrated in FIG. 8D, the incubation liner 250 may be positioned inboard of the motorized gearing and the one or more drawer rails while the specimen support surface 234 may be moved into and out of an interior space 252 defined by the incubation liner 250. The incubation liner 250 may be mounted to the faceplate interface 213 via fastener, magnets, or other coupling means.

FIG. 10 illustrates the incubation liner 250 in isolation. In some embodiments, in order to provide humidity control, the environmental control assembly 208 may include a fluid pump (not shown), which may pump fluid (e.g., water) into the interior space 252 of the incubation liner 250. In embodiments, a bottom surface 253 of the incubation liner 250 may be sloped at some acute angle relative to the back wall 254 of the incubation liner 250 to define a fluid reservoir 256 within the modular storage unit 202. One or more fluid sensors 261 (e.g., electrodes) may be mounted into the bottom surface 253 of the incubation liner 250 and communicatively coupled to the control unit 102 to provide a fluid level signal indicative of fluid levels within the modular storage unit 202. For example, the one or more fluid sensors 261 may include a first fluid sensor 261a, a second fluid sensor 261b, and a third fluid sensor 261c. Each of the sensors may be mounted within the fluid reservoir 256 at a position corresponding to fluid levels within the fluid reservoir 256 being full (e.g., P1), in need of refill (e.g., P2), and empty (e.g., P3). Accordingly, fluid at or above the first fluid sensor 261a may indicate that the fluid reservoir 256 is fully filled. Fluid levels between the second fluid sensor 261b and the third fluid sensor 261c may indicated that the fluid reservoir 256 should be refilled. Fluid levels below the third fluid sensor 261c may indicate that the fluid reservoir 256 is empty.

In embodiments, fluid tanks may be provided within the maintenance corridor 116 of the frame 110 of the storage assembly 100, and may be plumbed to the individual modular storage units through the environmental control assembly 208, including for example tubing, pumps, valves, or combinations thereof. The control unit 102 may be configured to operate the valves and/or pumps of the environmental control assembly 208 to refill the fluid reservoir 256 as needed.

To provide the desired humidity, heating of the incubation liner 250 may cause fluid within the fluid reservoir 256 to evaporate causing humidity levels to increase. The humidity sensor provided by the sensing platform 226, may provide feedback to the control unit 102, to allow the control unit 102 to precisely control humidity levels within the modular storage unit 202. In some embodiments, the incubation liner 250 may include a plurality of separately heated zones (e.g., sides, back, bottom, and/or top). That is, the control unit 102 may separately control different zones of the incubation liner 250 to provide fine-tuned control of temperature and/or humidity within the environment of the incubation liner 250. For example, a bottom heater (e.g., below the fluid reservoir 256), may be separately controlled from the other zones of the incubation liner 250 such that the bottom heater may be heated at a different rate. Accordingly, where humidity levels are to be increased, a temperature of the bottom heater may be raised to encourage evaporation within the fluid reservoir 256 while the remaining zones may be left unadjusted to maintain environmental air temperature.

It is noted that in some embodiments, the incubation liner 250 may not define a fluid reservoir 256. For example, the environmental control assembly 208 may include a bubbler system 270 that humidifies dry carbon dioxide to a relative humidity (e.g. about 90% RH at about 5% $CO_2$). For example, the bubbler system 270 may include a heated vessel 272 that holds a controlled volume of sterile (deionized or distilled) water. The heated vessel 272 may be heated up to about 60° C., for example. Dry carbon dioxide may be injected into the warmed water via, for example, a microporous aspirator generating humidified carbon dioxide that floats to the top and then is plumbed into the heated interior space 252 of the incubation liner 250. The humid carbon dioxide may then be recirculated via a small fan (not shown) within the chamber to maintain uniform carbon dioxide levels, relative humidity, and temperature. The fan be part of an air filtration system (e.g., a HEPA and/or ULPA filtration system) for particle capture and mitigation. In embodiments, the control unit 102 is communicatively coupled to the bubbler system 270 to adjust water temperature and carbon dioxide flow rate to meet desired environmental conditions. The bubbler system 270 may be mounted within the modular storage unit 202 enclosure 210, but outside of the incubation liner 250. In other embodiments, the bubbler system 270 may instead be located within the maintenance corridor 116 of the storage assembly 100 and plumbed to the enclosure 210 through the environmental control assembly. In some embodiments, humid air and dry carbon dioxide may be separate injected.

In any of the embodiments, an air filtration system (e.g., a HEPA and/or ULPA filtration system) may be incorporated inside of the modular storage unit. The air filtration system may recirculate air within the incubation liner 250 and may aid in maintaining a clean, dust free environment within the modular storage unit 202. Such air filtration system may be provided in addition to the above described air filtration system of the overall storage assembly 100.

In embodiments, gases may be injected into the modular storage unit 202 to provide particular air quality. While it is noted that carbon dioxide may be injected into the modular storage unit 202 through a bubbler system 270, (in addition or in alternative to the bubbler system 270) gasses may be directly introduced to the modular storage unit 202. For example, in some embodiments, different environment gasses may be stored in storage vessels (e.g., pressurized storage vessels) within the maintenance corridor 116 of the storage assembly 100. Depending on the desired environment, the control unit 102 may implement gas mixing (e.g., with a gas mixer within the maintenance corridor 116) to mix biological gasses such oxygen, carbon dioxide, nitrogen, and any combination thereof. The mixture may then be delivered into the modular storage unit 202 via the environmental control assembly 208. Such gas mixtures may provide aerobic, anaerobic, normoxic, hypoxic, or other environmental conditions. In other embodiments, biological gases may be premixed to satisfy the desired environmental conditions, stored in a pressurized vessel, and directly injected into the modular storage unit 202.

As noted above, each modular storage unit 202 may include an electrical communication harness 201 which allows the components of the modular storage unit 202 to be plugged into the control system 101 of the storage assembly 100, such that the control unit 102 of the storage assembly 100 may individually control the various operations of each modular storage unit 202. For example, the communication harness 201 may include a mini controller (e.g., mini PC), and communication, relay and input/output hardware for each of the controllable components of the modular storage unit 202. Communication through the communication harness 201 may allow the control unit 102 to precisely control all environmental temperatures of the incubation liner 250, gas flow rates, gas pressures, drawer actuations, and any communications with external hardware such as a biological printing platform, as described herein. The various connections may extend through the enclosure frame 212 (e.g., through the bottom or a back wall 254 of the enclosure frame 212) to allow for connection to the storage assembly 100.

Referring specifically now to FIGS. 9A-9C, when configured for perfusion, the modular storage unit 202 may additionally include one or more perfusion actuation platforms 280 and a perfusion pump/valve array 286 for delivery of perfusion media to the specimen holder 10. Embodiments may further include a perfusion media reservoir 288. In some embodiments the pump/valve array 286 may include sensors (e.g., flow and/or pressure sensors) that provide feedback to the control unit 102 for fine-tuned control of delivery and/or removal of the perfusion media to the specimen holder 10.

As noted herein, specimen holders 10 may include any structure configured to house a specimen therein including to, but not limited to well-plates, petri dishes, tissue culture flasks, test tubes, or the like. For perfusion, the specimen holder 10 may comprise a fluidic manifold assembly 20 that is fluidly plumbed to each compartment (or well) within the specimen holder 10. Such specimen holders are more fully described in U.S. patent application Ser. No. 16/135,299 filed Sep. 19, 2018, entitled "Well-Plate and Fluid Manifold Assemblies and Methods," hereby incorporated by reference in its entirety. As described therein, the fluidic manifold assembly 20 may provide a plurality of flow paths to delivery fluid into and/or of the plurality of wells. The fluidic manifold assembly 20 may provide inlet port(s) 22 (e.g., rubber port(s) for delivery of fluid and outlet ports 24 (e.g., rubber port(s) for removal of fluid from the wells of the well plate. Referring to FIGS. 13B and 13C, the fluid inlet port(s) 22 may be located along one side of the fluidic manifold assembly 20 and the outlet port(s) 24 may be located on the opposite side of the fluidic manifold assembly 20.

In embodiments, the fluid inlet ports and outlet ports correspond to rows of wells in the well-plate. Accordingly, each well within the row of wells may receive approximately the same media feed, flow rate, pressure, etc. For example, a 48 well plate may include eight rows of six wells. Accordingly, for discrete flow control, eight individual pumps, valves, inlets, outlets, and control channels may be provided for independent control of flow through each row. However, in additional embodiments, it is noted that each well or compartment within the specimen holder 10 may have discreet flow control for supply and waste. For example, in a well plate with 48 wells, 48 pumps, valves, inlets, outlets, and control channels may be provided for independent control of media flow to and from each well. In yet further embodiments the fluidic manifold may only include one inlet port and one outlet port to provide the approximately same flow of media throughout the entire well-plate.

For perfusion, the specimen holder 10 is positioned on the specimen support surface 234 of the drawer 231 with the fluidic manifold assembly 20 positioned thereon. Coupled to the drawer faceplate 232 (e.g., through bolts, pins, or other fastening means), may be the perfusion actuation platform 280. The perfusion actuation platform 280 may be any device configured to fluidically couple the specimen holder 10 to a media reservoir. For example, FIGS. 13B and 13C, illustrate a perfusion actuation platform 280. The perfusion actuation platform 280 may include a fluid inlet portion 281 and a fluid outlet portion 282. The fluid inlet portion 281 and the fluid outlet portion may be coupled to one another through one or more actuators 283 (e.g., pneumatic, mechanical (e.g., drive screws, belts, gears, etc.), hydraulic, or electric (e.g., via solenoids)), which may be operably coupled to the control unit 102 to allow operation of the one or more actuators 283 by the control unit 102.

The fluid inlet portion 281 may define a one or more inlet needles 290 (e.g., hypo-tubes) configured to be received within the inlet port(s) 22 of the fluidic manifold assembly 20 to fluidically coupled the fluidic manifold assembly 20 to the media reservoir 288. The fluid outlet portion 282 may define one or more outlet needles 292 (e.g., hypo-tubes) configured to be received within the outlet port(s) 24 of the fluid manifold assembly. The fluid outlet port may fluidically coupled the fluidic manifold assembly to a receptacle for receiving waste fluid. Depending on the number of inlet and outlet ports 22, 24 of the fluidic manifold assembly 20, the perfusion actuation platform 280 may be interchangeable to include a mating number of fluid inlet needles 290 and fluid outlet needles 292 to correspond to the particular fluidic manifold. During transfer of a specimen holder 10 and fluidic manifold assembly 20 into the drawer 231, the fluid inlet portion 281 and the fluid outlet portion 282 may be moved to an open position as illustrated in FIG. 13B to allow for placement of the specimen holder 10 and fluidic manifold assembly onto the specimen support surface 234. The drawer 231 may precisely position the specimen holder 10 and fluidic manifold assembly 20 in a closed state so that the perfusion actuator platform 280 can repeatedly interface with the inlet/outlet ports 22, 24 of the fluidic manifold assembly 20 to prevent any binding or potential for fluid leaks. Once in position, the control unit 102 may control the one or more actuators 283 to cause the fluid inlet portion 281 and the fluid outlet portion 282 to move to a closed position, as illustrated in FIG. 13C, such that the plurality of needles 290 of the fluid inlet portion 281 are received within the inlet ports 22 of the fluidic manifold assembly 20 and the plurality of needles 292 of the fluid outlet portion 282 are received in the outlet ports 24 of the fluidic manifold assembly 20.

It is noted that while the fluidic manifold assembly 20 is position on top of the specimen holder 10, in other embodiments, the fluid manifold assembly 20 may integrate with the specimen holder may for part of a bottom side of the specimen holder 10.

Referring again to FIG. 13A, a media reservoir 288 may be coupled to each modular storage units 200. In embodiments, the media reservoir 288 may be removable to allow for replacement and/or refill of the media reservoir with media (e.g., sterile culture media). In some embodiments, the media reservoir 288 may be a bottle (e.g., a GL45 250-500 mL bottle), a bag, a bladder, a jar, a syringe, a pipette, or the like. In embodiments wherein the media reservoir 288 includes a bottle, the bottle may be provided with a sterilized septum cap that interfaces with a septum needle, which may be fluidically plumbed to fluid inlet portion 281 of the perfusion actuation platform 280. In some embodiments, a media warmer 285 may be provided to warm the media before introduction to the specimen(s) within the specimen holder 10. In some embodiments, tubing (not shown) fluidically coupling the media reservoir to the fluid inlet portion 281 of the perfusion actuation platform 280 may be routed within or in close proximity to the incubation liner 250 such that heating of the incubation liner 250 pre-warms to media before introduction to the specimen(s). Fluid may be driven from the media reservoir 288 to the specimen holder 10 via the media pump/valve array 286 which is operatively coupled to the control unit 102 such that the control unit may independent operate the various pumps and/or valves of the media pump/valve array 286. Additionally flow and/or pressure meter and sensors may be implemented along the fluid line(s) (e.g., tubing, not shown) to monitor fluidic parameters prior to entering the fluidic manifold assembly 20 and specimen. It is noted that while the pump/valve array 286 is depicted as being placed outside of the incubation liner 250. In some embodiments, the pump/valve array may be positioned within the incubation liner 250.

In some embodiments, the media reservoir 288 may be provided with a reagent chiller to preserve the media at a cooler temperature within the reservoir until it is transferred to the specimen(s). This may allow the media to have a longer shelf life than if stored at room or elevated temperatures.

In some embodiments, a separate mixing station for mixing a wide variety of culture medias, additives, serums, particles, etc., can be provided that is fluidically coupled to the modular storage unit 202 (e.g., as part of the storage assembly 100). Using the user interface device 104, a user may programmatically add together the available ingredients to make a unique culture media blend based on, for example, desired growth requirements of a particular specimen.

It is noted that in embodiments, wherein the modular storage unit 202 is assembled for perfusion applications, the modular storage unit 202 may have a fewer number of drawers. Each drawer may be provided with a perfusion actuation platform 280. For example, in a unit having a first drawer and a second drawer, a first perfusion actuation platform would be provided to fluidically coupled a first specimen holder in the first drawer to a fluid media reservoir and a second perfusion actuation platform would be provided to fluidically couple a second specimen holder in the second drawer to a fluid media reservoir. The fewer number of drawers may provide additional space for the perfusion actuation platform(s) to be positioned within the modular storage unit 202. It is noted that larger modular storage units 200 may be configured to include a greater number of drawer and perfusion actuation platform assemblies. In some embodiments, modular storage units as described herein include at least two drawers that are independently controlled to move between an open and closed position by the control unit.

Figure 14:
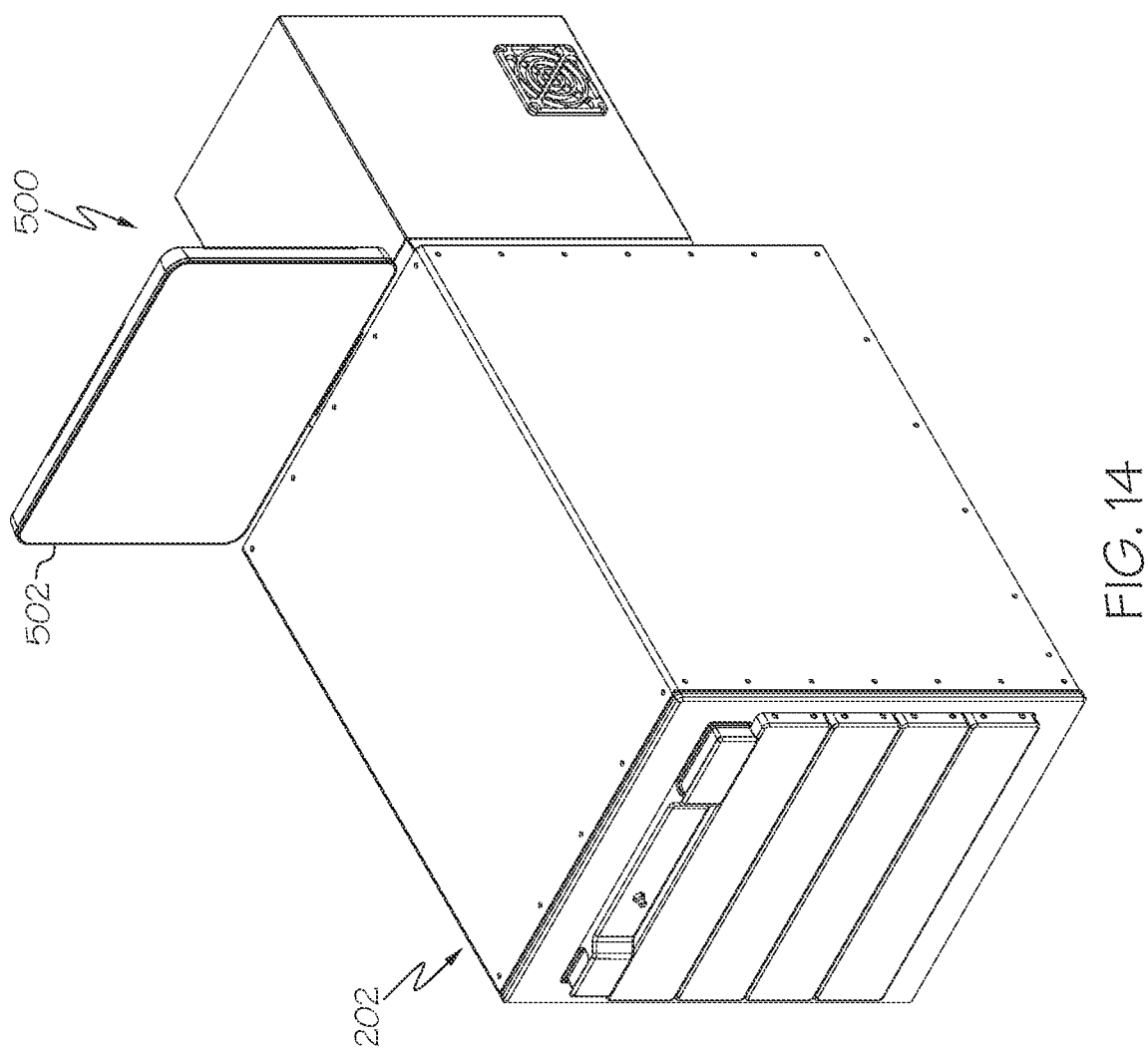
FIG. 14 depicts a modular storage unit a modular operation unit, according to one or more embodiments shown and described herein.

It is noted that while the modular storage units 202 as described herein can be assembled within the storage assembly 100 as an array, in some embodiments, the modular storage units 202 may be operated independently of the storage assembly 100 for benchtop use, for example. For example, with reference to FIG. 14, a modular storage unit 202 according to any of the embodiments described herein is depicted. A modular control unit 500 may be coupled to the electrical communication harness 201 to allow for operation of all functionality of the modular storage unit 202 in a small form factor. The modular control unit 500 may include an external power supply for providing power to the modular storage unit 202. In the illustrated embodiment, the modular control unit 500 includes a user interface device 502 (e.g., display, touchscreen, or the like) to allow a user to input instructions for operation of the modular storage unit 202. Accordingly, usage of the modular storage unit 202 is not limited to application with the storage assembly 100 described above.

In some embodiments, each modular storage unit 202 may have a unique identification chip that would be communicatively coupled to the control unit 102 when docked in the storage assembly 100, to allow the control unit to recognize and classify the modular storage unit for specific environmental control and feedback.

It is noted that by designing each modular storage unit to have the same mechanical and electrical form factor, the modular storage units may be swapped out for other versions/configurations. For example, and not limited to, multi-drawer standard height well-plate compartment, multi-drawer tall height well-plate compartment, multi-drawer petri dish compartment, multi-drawer tissue culture flask compartment, microfluidic Perfusion compartment, and combinations thereof.

It should now be understood that embodiments as described herein are directed to storage assemblies for an array of modular storage units. Additionally the array of modular storage units may configured for incubation and/or perfusion of one or more specimens stored therein. A user may adjust a base assembly of a modular storage unit for application in either perfusion or incubation environments. A storage assembly may include a frame that may support the array of modular storage units. Each of the modular storage units may be arranged and rearranged by the user as desired. Each of the modular storage units may be docked into a control system of the storage assembly to allow for centralized control and adjustment of an incubation or perfusion environment for each of the modular storage units, such that each modular storage unit may have a different incubation or perfusion environment. Additionally, the storage assembly may provide an automated robotic workflow wherein a user may input a preset workflow pattern, and the storage assembly may arrange and rearrange specimens among the plurality of modular storage units in accordance with the preset workflow pattern. In yet further embodiments, the storage assembly may be integrated into a biological printing platform, such that printed biological samples may be automatically transferred between the biological printing platform and the storage assembly. For example, the biological printing platform may print a biological sample (e.g., a 3D printed cellular structure) into a specimen holder (e.g., well-plate, petri dish, or the like), which may then be transferred automatically (e.g., by a robotic arm of the biological printing platform) to the storage assembly which may then store the specimen holder per user-programmed or preset instructions.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter.

Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A storage unit for perfusion of one or more specimens, the storage unit comprising:
   an enclosure;
   an automated drawer assembly comprising:
      a faceplate mounted to the enclosure; and
      one or more drawers comprising a drawer faceplate and an inlet port;
   one or more perfusion actuation platforms coupled to the drawer faceplate and comprising a fluid inlet portion, wherein the one or more perfusion actuation platforms are configured to fluidically couple one or more specimen holders positioned within the one or more drawers to a media reservoir by positioning the fluid inlet portion within the inlet port; and
   a control unit communicatively coupled to the automated drawer assembly to control opening and closing of the one or more drawers and to control fluidically coupling the one or more perfusion actuation platforms to the media reservoir.

2. The storage unit of claim 1, further comprising an incubation liner configured for heating and/or insulating the enclosure, wherein the incubation liner is communicatively coupled to the control unit.

3. The storage unit of claim 1, further comprising an environmental control assembly communicatively coupled to the control unit and configured to control humidity, temperature, biological gas concentrations, perfusion parameters, or combinations thereof.

4. The storage unit of claim 3, wherein the environmental control assembly comprises a bubbler system for humidifying dry carbon dioxide.

5. The storage unit of claim 1, wherein the faceplate is magnetically coupled to the enclosure.

6. The storage unit of claim 1, wherein:
   the one or more drawers comprise a first drawer and a second drawer; and
   the one or more perfusion actuation platforms comprise:
      a first perfusion actuation platform configured to fluidically couple a first specimen holder positioned within the first drawer to the media reservoir; and
      a second perfusion actuation platform configured to fluidically couple a second specimen holder positioned within the second drawer to the media reservoir.

7. The storage unit of claim 1, wherein a perfusion actuation platform of the one or more perfusion actuation platforms comprises:
   a fluid inlet portion for delivery fluid to a fluidic manifold assembly of a specimen holder;
   a fluid outlet portion for retrieval of waste fluid from the fluidic manifold assembly of the specimen holder; and
   an actuator coupled to the fluid inlet portion and the fluid outlet portion and configured to move the fluid inlet portion and the fluid outlet portion between a closed position and an open position.

8. A modular storage unit for incubation and/or perfusion of one or more specimens, the modular storage unit comprising:
   an enclosure;
   an automated drawer assembly comprising:
      a replaceable faceplate mounted to the enclosure, the replaceable faceplate defining a number of drawer ports; and
      one or more drawers corresponding to the number of drawer ports in the replaceable faceplate, the one or more drawers comprising a drawer faceplate and an inlet port;
   one or more perfusion actuation platforms coupled to the drawer faceplate and comprising a fluid inlet portion, wherein the one or more perfusion actuation platforms are configured to fluidically couple one or more specimen holders positioned within the one or more drawers to a media reservoir by positioning the fluid inlet portion within the inlet port
   a control unit communicatively coupled to the automated drawer assembly to control opening and closing of the one or more drawers; and
   an environmental control assembly communicatively coupled to the control unit and configured to control humidity, temperature, biological gas concentrations, perfusion parameters, or combinations thereof.

9. The modular storage unit of claim 8, wherein the environmental control assembly comprises an incubation liner configured for heating and/or insulating the enclosure.

10. The modular storage unit of claim 9, wherein the incubation liner defines a fluid reservoir and the incubation liner comprises one or more fluid sensors communicatively coupled to the control unit, wherein the one or more fluid sensors output a fluid level signal indicative of a fluid level within the fluid reservoir.

11. The modular storage unit of claim 10, wherein the environmental control assembly comprises a bubbler system for humidifying dry carbon dioxide.

12. The modular storage unit of claim 8, wherein the replaceable faceplate is magnetically coupled to the enclosure.

13. The modular storage unit of claim 8, wherein the one or more drawers comprises at least two drawers.

14. The modular storage unit of claim 8, further comprising a user interface device communicatively coupled to the control unit and configured to receive a user input to control operation of the modular storage unit.

15. A storage assembly for storing a plurality of specimens, the storage assembly comprising:
   a frame;
   a plurality of modular storage units for perfusion and/or incubation of one or more specimens removably coupled to the frame;
   a sample transfer apparatus configured to retrieve a specimen holder from a chosen modular storage unit of the plurality of modular storage units; and
   a control unit communicatively coupled to the sample transfer apparatus, wherein the control unit is configured to cause the sample transfer apparatus to retrieve a specimen from a modular storage unit of the plurality of modular storage units and deliver the specimen to a delivery position;

wherein the modular storage unit of the plurality of modular storage units comprises:
- an enclosure;
- an automated drawer assembly communicatively coupled to the control unit, the automated drawer assembly comprising:
  - a faceplate mounted to the enclosure; and
  - one or more drawers comprising a drawer faceplate and an inlet port;
- one or more perfusion actuation platforms coupled to the drawer faceplate and comprising a fluid inlet portion, wherein the one or more perfusion actuation platforms are configured to fluidically couple one or more specimen holders positioned within the one or more drawers to a media reservoir by positioning the fluid inlet portion within the inlet port.

16. The storage assembly of claim 15, wherein the frame defines an enclosure within which the plurality of modular storage units and the sample transfer apparatus are positioned.

17. The storage assembly of claim 15, wherein the plurality of modular storage units are arranged in an array comprising a plurality of rows and a plurality of columns.

18. The storage assembly of claim 15, wherein each of the plurality of modular storage units comprises an environmental control assembly communicatively coupled to the control unit and configured to control humidity, temperature, biological gas concentrations, perfusion, or combinations thereof.

19. The storage assembly of claim 15, wherein the sample transfer apparatus comprises:
- a gripping device configured to grip and release the specimen holder;
- a two dimensional gantry arranged to move the gripping device between a closed position for retrieving the specimen holder and a released position to release the specimen holder; and
- a conveyor configured to move the specimen holder when placed thereon by the gripping device to a position outside of the frame.

* * * * *